(12) United States Patent
Yamamoto et al.

(10) Patent No.: US 8,905,073 B2
(45) Date of Patent: Dec. 9, 2014

(54) MICRO FLUID DEVICE AND TRACE LIQUID DILUTING METHOD

(75) Inventors: Kazuki Yamamoto, Kyoto (JP); Hiroji Fukui, Osaka (JP); Minoru Seki, Tokyo (JP)

(73) Assignee: Sekisui Chemical Co. Ltd., Osaka (JP)

( * ) Notice: Subject to any disclaimer, the term of this patent is extended or adjusted under 35 U.S.C. 154(b) by 1129 days.

(21) Appl. No.: 12/282,168

(22) PCT Filed: Mar. 8, 2007

(86) PCT No.: PCT/JP2007/054518
§ 371 (c)(1),
(2), (4) Date: Dec. 19, 2008

(87) PCT Pub. No.: WO2007/105584
PCT Pub. Date: Sep. 20, 2007

(65) Prior Publication Data
US 2009/0126516 A1 May 21, 2009

(30) Foreign Application Priority Data

Mar. 9, 2006 (JP) ................................ 2006-063535
Mar. 9, 2006 (JP) ................................ 2006-064131

(51) Int. Cl.
*B01F 5/00* (2006.01)
*B01F 13/00* (2006.01)
(Continued)

(52) U.S. Cl.
CPC ..... *B01F 13/0071* (2013.01); *B01L 2400/0487* (2013.01); *B01F 15/0404* (2013.01);
(Continued)

(58) Field of Classification Search
USPC .............. 137/597, 896; 422/70, 100; 222/134
See application file for complete search history.

(56) References Cited

U.S. PATENT DOCUMENTS 6,004,515 A * 12/1999 Parce et al. .................. 422/504
6,409,832 B2 6/2002 Weigl et al.
(Continued)

FOREIGN PATENT DOCUMENTS

JP 2002-357616 A 12/2002
JP 2004-157097 A 6/2004
(Continued)

OTHER PUBLICATIONS

International Search Report for the Application No. PCT/JP2007/054518 mailed Jul. 3, 2007.
(Continued)

*Primary Examiner* — William McCalister
(74) *Attorney, Agent, or Firm* — Cheng Law Group, PLLC

(57) ABSTRACT

A microfluidic device provided with a micro-channel structure capable of easily and positively providing therein micro-droplet having various dilution ratios. A micro-channel structure provided in a substrate (2) has a first mixing unit (11) and a second mixing unit (21) connected to the downstream side of the first mixing unit (11), with each mixing unit (11, 21) having first through third micro-channels. One end of a first weighing unit (11d) consisting of a micro-channel having a capacity equivalent to the volume of a specified-amount first micro-droplet is opened to a first micro-channel (11a), and the other end is opened to a merging unit (12a) provided on a second micro-channel (12). One end of a second weighing unit (13d) consisting of a micro-channel having a capacity equivalent to the volume of a specified-amount second micro-droplet is connected to a third micro-channel (13), and the other end is opened to the merging unit (12a). Any one of the first through third outlet ports of the first mixing unit is connected with the first or the third inlet port of the second mixing unit (21).

4 Claims, 12 Drawing Sheets

(51) Int. Cl.
   *B01F 15/04* (2006.01)
   *B01L 3/00* (2006.01)
   *B01F 13/10* (2006.01)
   *G01N 35/00* (2006.01)
   *B01F 15/02* (2006.01)

(52) U.S. Cl.
   CPC .............. *B01F 2013/1052* (2013.01); *G01N 2035/00465* (2013.01); *B01L 2300/0816* (2013.01); *B01L 3/502792* (2013.01); *B01L 2200/0605* (2013.01); *B01J 2219/00889* (2013.01); *B01F 2015/0221* (2013.01); *B01L 2300/0867* (2013.01)
   USPC . 137/597; 137/896; 422/70; 222/134 CPC

(56) References Cited

U.S. PATENT DOCUMENTS

| | | | |
|---|---|---|---|
| 6,717,136 B2* | 4/2004 | Andersson et al. | 250/288 |
| 6,776,965 B2* | 8/2004 | Wyzgol et al. | 422/509 |
| 6,880,576 B2* | 4/2005 | Karp et al. | 137/806 |
| 7,036,917 B2* | 5/2006 | Muller-Chorus et al. | 347/84 |
| 7,134,453 B2* | 11/2006 | Peters et al. | 137/806 |
| 2002/0195463 A1 | 12/2002 | Seki et al. | |
| 2003/0077204 A1 | 4/2003 | Seki et al. | |
| 2003/0166265 A1* | 9/2003 | Pugia et al. | 435/288.3 |
| 2003/0198576 A1* | 10/2003 | Coyne et al. | 422/100 |
| 2004/0096358 A1* | 5/2004 | Blankenstein et al. | 422/58 |
| 2004/0209381 A1* | 10/2004 | Peters et al. | 436/177 |
| 2004/0258569 A1 | 12/2004 | Yamazaki et al. | |

FOREIGN PATENT DOCUMENTS

| | | |
|---|---|---|
| JP | 2004-163104 A | 6/2004 |
| JP | 2005-017057 A | 1/2005 |
| JP | 2005-147957 A | 6/2005 |
| JP | 2006-023209 A | 1/2006 |
| JP | 2006-046605 A | 2/2006 |
| JP | 2007-279068 A | 10/2007 |
| WO | WO 2007/105584 A1 | 9/2007 |

OTHER PUBLICATIONS

Notification of Reasons for Refusal for the Application No. 2007-189914 from Japan Patent Office mailed May 7, 2008.
Notification of Reasons for Refusal for the Application No. 2007-534932 from Japan Patent Office mailed May 7, 2008.
Supplementary European Search Report for the Application No. EP 07 73 8009 dated Apr. 21, 2010.

* cited by examiner (a)

(b)

(a)

(b)

(c)

(a)

(b)

MICRO FLUID DEVICE AND TRACE LIQUID DILUTING METHOD

TECHNICAL FIELD

The present invention relates to a microfluidic device having a micro-channel structure, formed in a substrate, for mixing a micro-droplet, and in more detail, the present invention relates to a microfluidic device used for mixing or diluting samples, reagents, etc. for various analyses.

BACKGROUND ART

Conventionally, samples and reagents are often diluted in analysis for samples and in chemical reaction of various substances. Especially, in the case of dilution of trace amount of liquid, an operation method using a microplate and distributive pouring pipette or a method of using a dispensable robot device has been used. On one hand, the operation method using a microplate and a distributive pouring pipette have needed a complicated operation and an experienced experimenter. Furthermore, simple mixing operation of samples and reagents has been difficult outside of the laboratory or in a bedside for clinical laboratory test, etc.

On the other hand, dilution methods using dispensable robot devices inevitably need large-sized apparatuses, also failing in providing simpler use outdoors, in a bedside, etc.

In recent years, microfluidic devices receive attention as analysis devices for handling trace amount of liquid. The microfluidic devices have a substrate with a size, for example, providing easier portability and easier handling. This substrate has a micro-channel structure formed therein for transporting samples, reagents, diluted solutions, etc. The above-described micro-channel structure suitably has reagent storing section, sample delivering section, diluting solution storing section, reaction chamber, mixing section, etc.

The above-described microfluidic device is usually formed using a substrate having a plane area not more than several hundreds of square centimeters, the substrate having a thickness of approximately 0.5 to 10 mm. Furthermore, the diameter of the flow path of the above-described micro-channel structure usually has an extraordinary fineness of approximately 5 micrometers to 1 mm. Here, when the flow path has a flat structure, the diameter of the micro-channel is specified by a width of the narrower width of the cross section of the first flow path. Incidentally, micro-droplets to be transported is sent with air etc., and often have a liquid drop-like shape.

Accordingly, since the micro-droplet will be transported through a micro-channel with a very small width in case of dilution of the samples and the reagents in the above-described microfluidic device, the surface tension of the micro-droplet, the wettability of the wall surface of the micro-channel, etc. have significant influence in contrast with normal flow paths for liquids to be transported. In addition, quantitative measuring of such a small amount of micro-droplet is difficult, resulting in possible problem of the necessity for complicated flow path circuit pattern.

Following patent document 1 discloses a method of forming a proteinic crystal in a laminar flow using a microfluidic device. In addition, following nonpatent document 1 discloses a method of forming a crystal from a trace amount of liquid by strict temperature control in a microfluidic device.

However, the patent document 1 and the nonpatent document 1 describe that each method described has a very small reaction field, and thereby enables highly precise control of reaction, but the methods has a problem that the introducing method of a protein solution to a crystallization section cannot provide a small dead volume.

The following patent document 2 discloses a trace amount of liquid measuring structure enabling measuring of a very small amount of liquid only by a simpler structure and a simpler operation for solving the above described problems. The trace amount of liquid measuring structure described in the patent document 2 has a trace fluid measuring structure using a passive valve. This trace fluid measuring structure has a first micro-channel and a second flow path extending in a predetermined direction, respectively; a third flow path having an opening in a passage wall of the first micro-channel; and a fourth flow path that has an opening in a passage wall of the second flow path, and that connects an end of the third flow path and the second flow path, the fourth flow path being thinner than the first to the third flow path. The fourth flow path has a lower wettability as compared with that of the second flow path and the third flow path, or exhibits a relatively lower capillary force. And after a liquid introduced into the first micro-channel is sucked into the third flow path through an opening of the third flow path in a passage wall of the first micro-channel, the above-described liquid remained in the first micro-channel is removed, allowing measuring of the liquid with a volume corresponding to the capacity of the third flow path.

Patent document 1: U.S. Pat. No. 6,409,332 specification
Patent document 2: JP,2004-163104,A
Nonpatent document 1: "Analytical Chemistry" (2002), 74, p.3505-3512

DISCLOSURE OF THE INVENTION

However, the microfluidic device provided with the trace amount of liquid measuring structure described in the patent document 2 has a problem that larger mixture ratios set as not less than 10 times fail to provide mixing exhibiting accuracy and excellent reproducibility. Conversely, in some cases, there may be necessities for dilution in graduated high magnifications like 10 times, 100 times, and 1000 times of samples or reagents in operation of analysis and reaction.

However, conventionally, the kind of microfluidic devices failed to work as micro-channel structures having a plurality of mixing units in a plurality of stages connected with each other. The reasons will be described as follows. In this kind of microfluidic devices, since an extremely small amount of micro-droplet is transported in a form like a drop within an extremely small flow path, and measuring and merging are performed using influence of a surface tension, wettability to the passage wall surface, and capillary phenomenon of the micro-droplet, the operation is based on the premise that the timings of extrusion of a plurality of measured micro-droplets from measuring sections to a merging section is coincident. However, in a connected system of a plurality of mixing units, since there is restriction that the second mixing unit will use the output of the first mixing unit, the timings of extrusion of a plurality of micro-droplets measured within the second mixing unit to a merging section from the measuring sections cannot be coincident. For this reason, simple connection of the first and the second mixing unit failed to provide proper operation of the second mixing unit. Therefore, concurrent construction of dilution series including mixed solution of various dilution ratios in microfluidic device was very difficult. Microfluidic devices fulfilling such requests is not yet developed until nowadays.

In addition, conventional dilution methods include methods of preparation of a diluted solution by adding at once and mixing a large amount of a buffer solution into a solution to be diluted, and multi-stage dilution methods by sequentially diluting a solution in several steps etc. Especially, the multi-stage dilution method has been used for preparation of a solution having a high dilution ratio with isoconcentration. In such dilution operation, quantitative sampling and mixing of a solution are practicable using normal methods. However, in order to prepare a uniform solution having a high dilution ratio within a microfluidic device, a multi-stage dilution method needed to be realized within the microfluidic device. In order to finally obtain a solution having a high dilution ratio by the multi-stage dilution with such an accurate concentration, there were needed 1) accurate measuring of a solution to be diluted and the buffer solution, and 2) uniform mixing of the solution to be diluted and the buffer solution. However, it was an extremely difficult problem to complete these operation within the microfluidic device.

In consideration of the present circumstances of the above-described conventional technology, an object of the present invention is to provide a microfluidic device having a micro-channel structure that allows not only measuring of a plurality of micro-droplets in a high precision, but allows mixing of the plurality of micro-droplets, and easier and more reliable preparation of micro-droplets with various dilution ratios.

The microfluidic device according to the present invention comprising: a substrate; and a micro-channel structure through which the micro-droplet is transported, the micro-channel structure being formed in the substrate, wherein the micro-channel structure has a first mixing unit, and a second mixing unit connected to a downstream of the first mixing unit. Each mixing unit comprises: a first measuring section consisting of a micro-channel having a capacity equal to a volume of a first micro-droplet having a fixed amount, for measuring of the fixed amount of the first micro-droplet; a second measuring section consisting of a micro-channel having a capacity equal to a volume of a second micro-droplet of a fixed amount, for measuring the fixed amount of the second micro-droplet; a merging section for merging the first and the second micro-droplets that have been measured in the first and the second measuring section; a mixing section for mixing the first and the second micro-droplets, the mixing section connected in series to a downstream of the merging section; an exhausting section for exhausting the mixed droplet obtained by mixing the first and the second micro-droplets; a first to a third inlet ports and a first to a third outlet ports; the first micro-channel for connecting the first inlet port and the first outlet port;

a second micro-channel having the merging section, the mixing section, and the exhausting section, the second micro-channel connecting the second inlet port and the second outlet port; a third micro-channel for connecting the third inlet port and the third outlet port, an end of the first measuring section being connected to the first micro-channel, an other end having an opening in the merging section provided in the second micro-channel, an end of the second measuring section being connected to the third micro-channel, an other end having an opening in the merging section provided in the second micro-channel, the second outlet port being connected to the exhausting section, one of the outlet ports in the first to the third outlet ports of the first mixing unit being connected to the first or the third inlet port of the second mixing unit.

In a certain specific aspect of the microfluidic device concerning the present invention, the second outlet port of the first mixing unit is connected to the first or the third inlet port of the second mixing unit, and thereby a micro-droplet mixed in the first mixing unit is used as a fixed amount of first or the second micro-droplet in the second mixing unit. In this case, the above described connection between the first mixing unit and the second mixing unit can provide a dilution series with a higher magnification.

Alternatively, in an other specific aspect of the microfluidic device concerning the present invention, the first outlet port of the first mixing unit is connected to the first inlet port of the second mixing unit, and the third outlet port of the first mixing unit is connected to the third inlet port of the second mixing unit. In this case, since the first and the second mixing unit are connected in parallel, a plurality of micro-droplets having the same dilution ratio may easily be obtained by similarly configuring the first and the second measuring section of the first and the second mixing unit. Alternatively, when different dilution ratios with each other are given with respect to the first mixing unit and the second mixing unit, micro-droplets having different dilution ratios with each other may also be obtained.

In the microfluidic device concerning the present invention, at least one of the third mixing unit may further be connected in the downstream of the second mixing unit, and thereby micro-droplets having a larger quantity of or a larger number of dilution ratios may easily be obtained In a further specific aspect of the microfluidic device concerning the present invention, an outlet opening of the first measuring section and an outlet opening of the second measuring section are disposed facing with each other in the merging section of the first and/or the second mixing unit.

Here, in the first and/or the second mixing unit, the outlet opening of the first measuring section and the outlet opening of the second measuring section may be disposed in different positions with each other in a flowing direction of the micro-droplet in the merging section.

A distance between the outlet opening of the first measuring section and the outlet opening of the second measuring section, in the flowing direction of the micro-droplet in the second micro-channel is preferably selected so as to avoid formation of air bubbles between the first micro-droplet supplied to the merging section from the first measuring section and the second micro-droplet supplied to the merging section from the second measuring section, and so as to avoid contact of the first and the second micro-droplet to the outlet opening of the second measuring section, or to the outlet opening of the first measuring section upon exhausting at different timings of the first and the second micro-droplet to the merging section from the second measuring section. In this case, even when the first and the second micro-droplet are exhausted at different timings to the merging section from the first and the second measuring section, air bubbles may hardly be involved, leading to reliable merging of the first and the second micro-droplet in the merging section.

The width of the second micro-channel in the merging section is preferably designed larger than a dimension along with the width direction of the above-described flow path of the exhausted micro-droplet, so that a micro-droplet, exhausted from the measuring section having the outlet opening located in the downstream in the merging section out of the first and the second measuring section, has a dimension for avoiding arrival to a wall surface on a side opposite to the side of outlet opening of the measuring section. Also in this case, there may hardly be caused involvement of air bubbles between the first micro-droplet exhausted from the first measuring section, and the second micro-droplet exhausted into merging section from the second measuring section.

In the microfluidic device concerning the present invention, it is preferred that the wall surface of both sides in a width direction of the flow path is designed to have an unsymmetrical shape, and/or the wall surface of both sides in a height direction of the flow path of the substrate is designed to have an unsymmetrical shape, in the mixing section. In this case, since the micro-droplet has different flowing states with each other on one side and on the other side, on at least one side of the both sides in the width direction of the flow path, and on at least one side of the both sides in the height direction of the substrate, in the mixing section, swirls may occur in the micro-droplet, resulting in more uniform mixing of the first and the second micro-droplet.

In a further specific aspect of the microfluidic device concerning the present invention, there are further provided with a first micro pump device for supplying a gas for transporting the first and the second micro-droplet into the merging section, the first micro pump device is connected to the second inlet port, and a second and a third micro pump device connected to the first and the third micro-channel, respectively, in order to measure a fixed amount of the micro-droplet in the first and the second measuring section, and in order to exhaust the first and the second micro-droplet to the merging section from the first and the second measuring section.

Driving of the first to the third micro pump devices allows measuring of the first and the second micro-droplets in the first and the second measuring section, and can exhaust them to the merging section, and furthermore can transport the exhausted first and second micro-droplets to the mixing section side.

In a further specific aspect of the microfluidic device concerning the present invention, a flow path opening and closing mechanism provided in the substrate in relation to at least one micro-channel is further provided in order to realize a condition where a flow of the micro-droplet is allowed in each micro-channel, and a condition where transportation of the micro-droplet is stopped in at least one micro-channel, the flow path opening and closing mechanism allowing movement of the micro-droplet within the micro-channel while the micro-channel is in an open state, and stopping movement of the micro-droplet while the micro-channel is in a closed state. Therefore, driving of the above-described flow path opening and closing mechanism can allow liquid sending within micro-channel, or can stop liquid sending for the micro-droplet. The flow path opening and closing mechanism preferably has a stopper allowing a shift between the open state and the closed state, and a stopper driving device allowing a shift of the stopper between the open state and the closed state. In this case, driving of the stopper driving device provided in the substrate raises a gas pressure in the flow path in the near side of the measuring section, and pushes out the micro-droplet from the measuring section to the mixing section.

A trace amount of liquid dilution method concerning the present invention is a trace amount of liquid dilution method using the microfluidic device configured according to the present invention. The method for obtaining a first and a second diluted solution of sample having different concentrations with each other comprises: a process for measuring the first micro-droplet in the first or the second measuring section of the first mixing unit as a sample, and for measuring the second micro-droplet as a diluting solution in the second or the first measuring section; a process for mixing the first micro-droplet as the sample and the second micro-droplet as a diluting solution, and fox exhausting the first diluted solution of sample as the mixed droplet in the first mixing unit; a process for measuring at least a part of the first mixed droplet exhausted from the first mixing unit in the first or the second measuring section of the second mixing unit, and for measuring a diluting solution as the second or the first micro-droplet in the second or the first measuring section of the second mixing unit; a process for obtaining the second diluted solution of sample as the second mixing micro-droplet by mixing the first diluted solution of sample and the diluting solution in the second mixing unit, and for exhausting the second diluted solution of sample as the second micro-droplet from the exhausting section of the second mixing unit.

In a specific aspect of the trace amount of liquid dilution method concerning the present invention, provided is the trace amount of liquid dilution method according to claim 13 is provided, wherein at least one of the third mixing unit is connected in the subsequent stage of the first and the second mixing unit for obtaining at least 3 diluted solutions of sample having different concentrations with each other.

In an other specific aspect of the trace amount of liquid dilution method concerning the present invention, n−2 of mixing units (n is a natural number not less than 3) are connected in the subsequent stage of the first and the second mixing unit, mixed micro-droplets as each diluted solution of sample are exhausted from the exhausting section of each mixing unit, and thereby n kinds of diluted solutions of sample having each different concentration is obtained.

EFFECT OF THE INVENTION

The microfluidic device concerning the present invention has a micro-channel structure formed in the substrate. The micro-channel structure has a first mixing unit, and a second mixing unit connected to the downstream of the first mixing unit. Since a first and a second micro-droplets supplied from a first and a second measuring section are merged in a merging section, and then they are mixed in a mixing section in each mixing unit, the mixed droplet obtained by mixing the first and the second micro-droplets having been exhausted from the first and the second measuring sections may be removed out in each of the mixing unit. Furthermore, since either of outlet ports of the first to the third outlet ports of the first mixing unit is connected to one or both of the first or the third inlet port of the second mixing unit, the mixed droplet may be obtained from the first and the second mixing units, respectively, or the mixed droplet having each different concentration may be obtained as the mixed droplet by diluting the second or the first micro-droplet with the first or the second micro-droplet, in each mixing unit.

Accordingly, a plurality of diluted micro-droplets, and diluted micro-droplets having a plurality of kinds of concentrations may easily and promptly be prepared in a microfluidic device configured using a single substrate.

Especially, since the micro-droplet mixed by the first mixing unit is used as a fixed amount of the first or the second micro-droplet in the second mixing unit, when the second outlet port of the first mixing unit is connected to the first or the third inlet port of the second mixing unit, a micro-droplet diluted at a higher magnification may be obtained in the second mixing unit.

Conventionally, micro-channel structures with a plurality of stages having a plurality of mixing units connected with each other have not been adopted in this hind of microfluidic devices. The reason is as follows. In this kind of microfluidic devices, an extremely small amount of micro-droplet is transported in a drop-like form in an extremely small flow path, and measuring and merging of the micro-droplet are carried out using the surface tension of the micro-droplet and the influence of wettability and capillary phenomenon of the wall surface of the flow path, and therefore there must be satisfied a premise that the timings of extrusion between a plurality of measured micro-droplets from the measuring sections to the merging section are to be concurrent. However, the connection of a plurality of mixing units had restrictions that the second mixing unit used the output of the first mixing unit, and as a result synchronization between the timings of extrusion of a plurality of micro-droplets measured within the second mixing unit to the merging section from the measuring section of could not be achieved, and therefore only a simple connection between the first second mixing units failed to allow proper function of the second mixing unit.

Alternatively, in the present invention, since investigations for exhibiting function as a mixing unit have been carried oat even in case where the timings between extrusion of a plurality of micro-droplets from the measuring section to the merging section are not concurrent, the second mixing unit can exhibit proper function even in a structure having connected the above-described first and second mixing unit. Accordingly, various combination of a plurality of mixing units is possible, and thereby quick and accurate transportation of micro-droplets mixed in each combination will be possible.

The device according to the present invention is suitable for use in various analyses and chemical reactions that need multi-stage mixing and dilution at different mixture ratios. Quicker preparation of micro-droplets having various concentrations, or a large numbers of micro-droplets in the microfluidic device will enable automation of operations needed for analyses and reactions and shortening of operation period of time.

DESCRIPTION OF NOTATIONS

Figure 1:
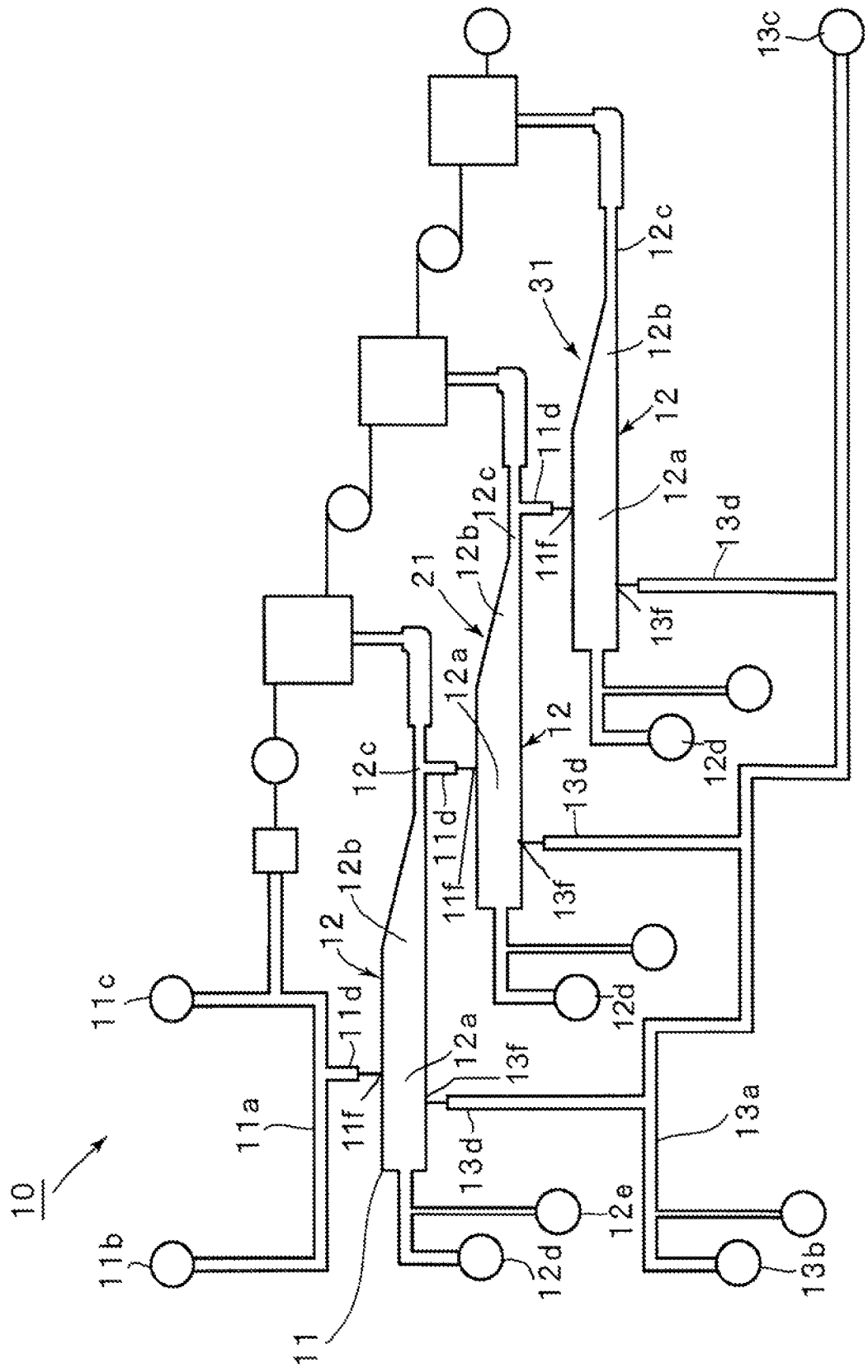
FIG. 1 is a plan view schematically illustrating a micro-channel structure of a microfluidic device according to one embodiment of the present invention.

1—microfluidic device
2—substrate
3—base plate
4 to 6—intermediate plate
4a—exhaust hole
5a—opening
6a—through hole
7—top plate
8—gas generating chamber
9—optical responsive gas generating component
10—micro-channel structure
11—the first mixing unit
11a—the first micro-channel
11b—gas supply hole
11c—pinhole as microfluid inlet port
11d—the first measuring section
11e—micro-channel for connection
11f—opening
12—the second micro-channel
12a—merging section
12b—mixing section
$12b_1$, $12b_2$—wall surface
12c—exhausting section
12d—gas supply hole
12e—gas exhausting hole
13a—the third micro-channel
13b—gas supply hole
13c—liquid supply hole
13d—the second measuring section
13e—micro-channel for connection
13f—opening
14a—the first micro-droplet
14b—the second micro-droplet
21—the second mixing unit
31—the third mixing unit
41—viscoelastic stopper
42—stopper drive 40—micro-channel opening and closing mechanism
43a-43c—circular part
62 to 66—flow path opening and closing mechanism
71—storing chamber
91, 92—mixing unit
93—flow path opening and closing mechanism
104a-104c—storing chamber
111,121—mixing unit
111a—micro-channel
111d, 121d—measuring section
113a—micro-channel
113d, 123d—measuring section
112,122—micro-channel
131,132—storing chamber

BEST MODE FOR CARRYING OUT THE INVENTION

Hereinafter, the present invention will be described with reference to detailed embodiments and drawings of the present invention.

Figure 2:
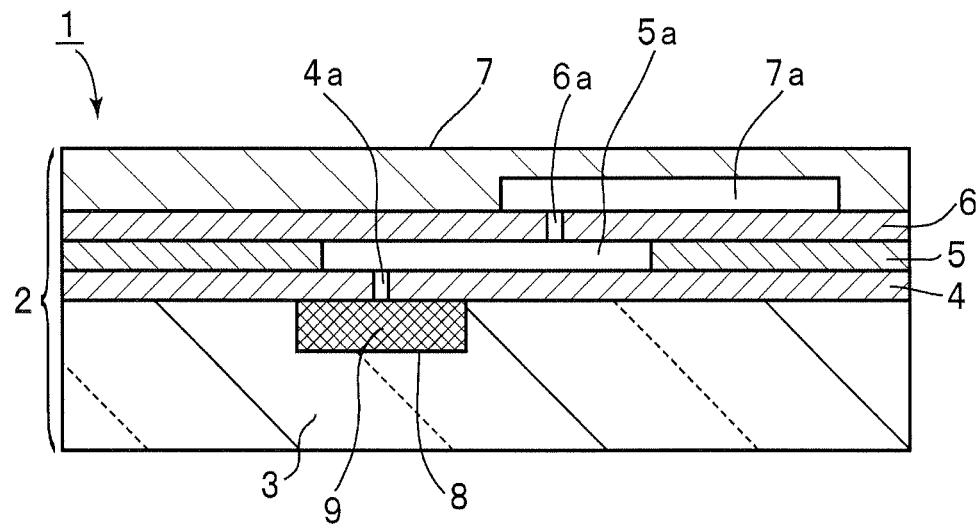
FIG. 2 is a front sectional view schematically illustrating a part of a microfluidic device according to one embodiment of the present invention.

FIG. 1 is a schematic plan view illustrating a micro-channel structure of a microfluidic device concerning an embodiment of the present invention, and FIG. 2 is a front sectional view illustrating schematically a part of a microfluidic device of the embodiment.

As illustrated in FIG. 2, a microfluidic device 1 has a substrate 2. The substrate 2 has a structure having a transparent base plate 3, intermediate plates 4 to 6, and a top plate 7 laminated therein. A gas generating chamber 8 is provided in the base plate 3. The gas generating chamber 8 has an opening on the upper surface of the base plate 3, and a gas generating component 9 for generating a gas responsive to irradiation of a light or heating is stored in the gas generating chamber 8. Storing of the responsive gas generating component 9 in the above-described gas generating chamber 8 forms a micro pump device as a source of drive for driving the micro-droplet. In consideration of easier control of the amount of the generated gas, an optical responsive gas generating component for generation of the gas by irradiation of a light is suitably used as the responsive gas generating component.

Since the base plate 3 has transparency, irradiation of a light from under surface side of the substrate 2 allows generation of the gas from the optical responsive gas generating component 9. This gas serves as a pressure source for driving the micro-droplet in the micro-channel mentioned later.

The above-described optical responsive gas generating component 9 is not in particular limited, and suitable optical responsive compositions that generate a gas by irradiation of a light may be used. For example, compositions including binder resins and gas generating agents that generate a gas by decomposition caused by irradiation of a light may suitably be used as such optical responsive compositions. Such gas generating agents include, for example, azido compounds, azo compounds, compounds of polyoxyalkylene resins and photoacid generators, and sodium hydrogencarbonate etc.

An exhaust hole 4a for exhausting the gas is formed in the intermediate plate 4. The exhaust hole 4a passes through from the under surface to the upper surface of the intermediate plate 4, and an open lower end thereof faces the gas generating chamber 8.

An opening 5a passing through the intermediate plate 5 is provided in the intermediate plate 5. This opening 5a provides a part of the micro-channel of the micro-channel structure. Furthermore, a through hole 6a opening to the opening 5a is formed in the intermediate plate 6. The upper opening of the through hole 6a is opened to a micro-channel 7a formed in the under surface of the top plate 7. This micro-channel 7a forms the micro-channel structure together with the above-mentioned opening 5a and the through hole 6a.

The above-described intermediate plates 4 to 6 and the top plate 7 are made of suitable plastic sheets or synthetic resins.

FIG. 2 schematically illustrates a part where a micro pump device for generation of a gas pressure for driving the micro-droplet is formed, and a part of the micro-channel structure in the above-described microfluidic device 1. The micro-channel of the microfluidic device is disclosed in the patent document 3 etc. mentioned above.

In general, the microfluidic device 1 has a size allowing portability as mentioned above, and it is configured using a small substrate 2 having a plane area not more than several hundreds cm$^2$, and preferably not more than 100 cm$^2$. Furthermore, the thickness of the substrate 2 is approximately 0.5 to 10 mm. And, not only driving part for transporting the above-described micro-droplets, but various micro-channels for transporting samples and micro-droplets as a diluting solution are formed in the substrate 2. Usually, such micro-channel structure includes a delivering section for supplying a sample and a diluting solution, a mixing section for mixing them, a reaction section for making them react, etc. The above-described delivering section, mixing section, and reaction section etc. are formed as a space having a certain amount of volume in the substrate 2, and they are disposed in an order in the small micro-channel, for example, the micro-channel 7a etc.

A special feature of the microfluidic device 1 of the embodiment is that the micro-channel structure 10 illustrated in FIG. 1 in a schematic plan view is formed in the substrate 2. The micro-channel structure 10 has the first mixing unit 11 and the second mixing unit 21 as indispensable components. The second mixing unit 21 is connected in a downstream part of the first mixing unit 11. Furthermore, in the present embodiment, another third mixing unit 31 is further connected in a downstream part of the second mixing unit 21.

Figure 3:
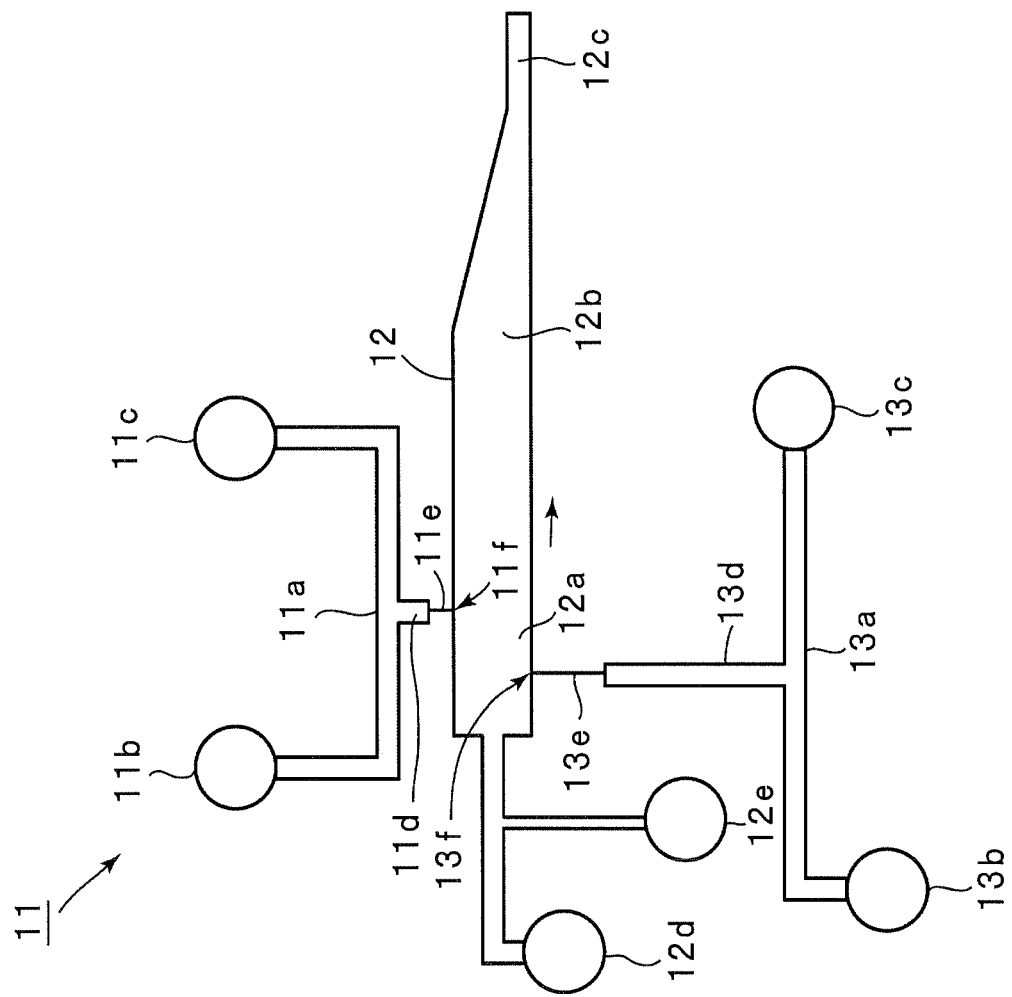
FIG. 3 is a schematic plan view for describing the first mixing unit in the micro-channel structure of embodiment illustrated in FIG. 1.

More detailed description of configuration of the first mixing unit 11 will be given with reference to the schematic enlarged plan view of FIG. 3.

The first mixing unit 11 has a first micro-channel 11a. A gas supply hole 11b is connected to an end of the first micro-channel 11a. A first pinhole as microfluid inlet port 11c, which can serve as the first inlet port (the inlet port of the first micro-channel 11a) of the first mixing unit 11 (see, for example, the embodiment shown in FIG. 1), is connected to another end of the first micro-channel 11a. The first micro-droplet supply hole 11c has an opening to the exterior of the substrate 1. This is a part for supplying the first micro-droplet to the micro-channel structure of the substrate 1.

The gas supply hole 11b is connected to of a gas generation drive source, such as the above-mentioned micro pump device, and can be opened and closed suitably.

The second micro-channel 12 is disposed in parallel with the first micro-channel 11a. The micro-droplet flows in the arrow direction in the second micro-channel 12. The merging section 12a is provided in the upstream, and the mixing section 12b is provided in the downstream. The exhausting section 12c is provided in series in the downstream of the mixing section 12b. That is, the exhausting section 12c is connected to a downstream end of the mixing section 12b with said downstream end able to serve as the second outlet port (the outlet port of the second micro-channel 12) (see, for example, each of the first, second, and third mixing units 11, 21, and 31 of FIG. 1).

Furthermore, the third micro-channel 13a is provided in a side opposite to a side, in which the first micro-channel 11a is provided, of the second micro-channel 12. One end of the third micro-channel 13a is connected to the respective gas supply hole 13b, and another end is connected to the respective liquid supply hole 13c, which can serve as the third inlet port (the inlet port of the third micro-channel 13a) of the mixing unit(s) (see, for example, each of the first, second, and third mixing units 11, 21, and 32 of FIG. 1). The gas supply hole 13b and the liquid supply hole 13c are configured in the same manner as the gas supply hole 11b and the microfluid inlet port 11c.

In addition, the first micro-channel 11a of the first mixing unit 11 comprises a first measuring section 11d consisting of a micro-channel branched from a main micro-channel of the first micro-channel 11a. The capacity of the first measuring section 11d is set equal to the volume of the micro-droplet to be measured.

Similarly, the third micro-channel 13a comprises a second measuring section 13d consisting of a micro-channel branched from a main micro-channel of the third micro-channel 13a, that has a fixed amount of capacity.

The capacity of the second measuring section 13d is set equal to the volume of the micro-droplet to be measured by the second measuring section 13d.

Accordingly, one end of the first, and the second measuring sections 11d and 13d is connected to the first micro-channel 11a and the third micro-channel 13a, respectively, and another end has an opening with respect to the merging section 12a provided in the second micro-channel 12, respectively. Please note that in embodiments with more than one mixing units, the first measuring section 11d can serve as the first micro-channel for mixing unit(s) positioned downstream (see, for example, the second and third mixing units 21 and 31 in the embodiment shown in FIG. 1; that is, in the second and third mixing units 21 and 31 of FIG. 1, the end of the first measuring section 11d that is open to the second micro-channel 12 of the preceding mixing unit 11 and 21 can serve as the first inlet port (i.e. the inlet port of the first micro-channel 11d) of the second and third mixing units 21 and 31, respectively).

Incidentally, the capacity of the above-described first and the second measuring section 11d and 13d is not especially limited, and they are usually set as an extremely small volume on the order of pico liter to micro liter. That is, as described above, the microfluidic device of the present invention enables transportation of such micro-droplets having an extremely minute capacity in the micro-channel A gas supply hole 12d can serve as the second inlet port (the inlet port of the second micro-channel 12) of the mixing unit(s) (see, for example, each of the first, second, and third mixing units 11, 21, and 31 in the embodiment shown in FIG. 1), and a gas exhausting hole 12e are disposed in the upstream of the second micro-channel 12. The gas supply hole 12d and a gas exhausting hole 12e are configured in the same manner as the gas supply hole 11b and the microfluid inlet port 11c.

Figure 5:
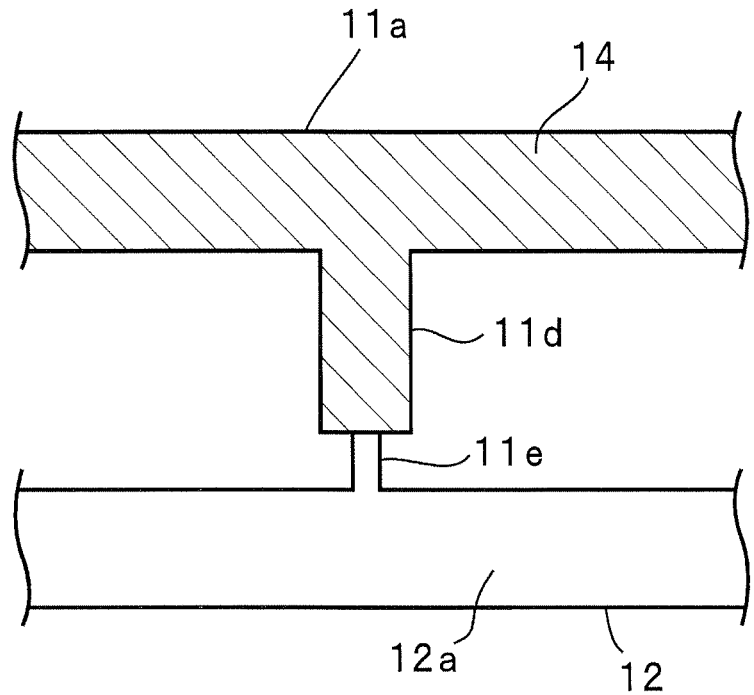
FIG. 5 is partial cross-sectional enlarged plan view for describing a process of measuring a fixed amount of the first micro-droplet for the first measuring section of embodiment illustrated in FIG. 1.
Figure 6:
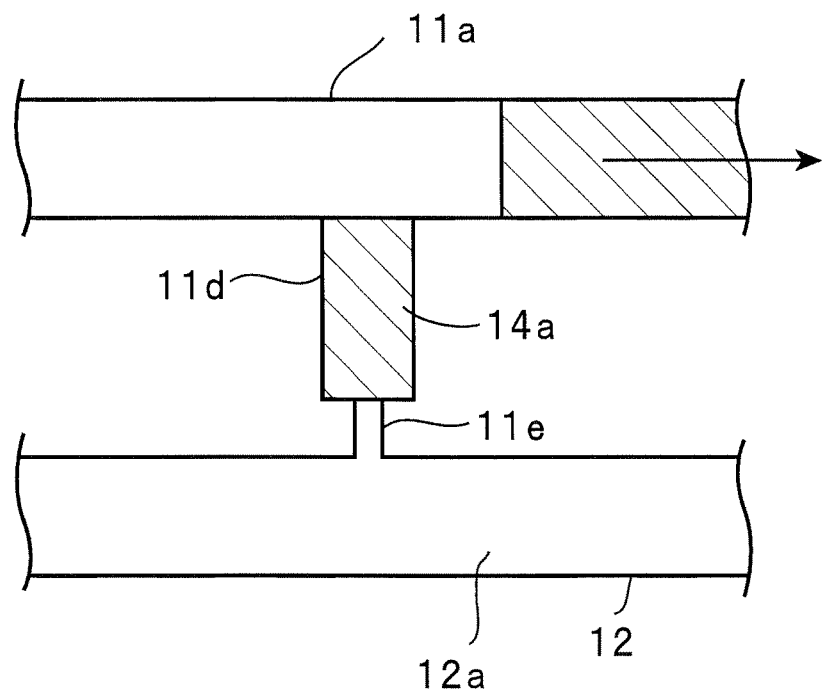
FIG. 6 is a partial cross-sectional enlarged plan view for describing a process of measuring a fixed amount of the first micro-droplet for the first measuring section in embodiment illustrated in FIG. 1.
Figure 7:
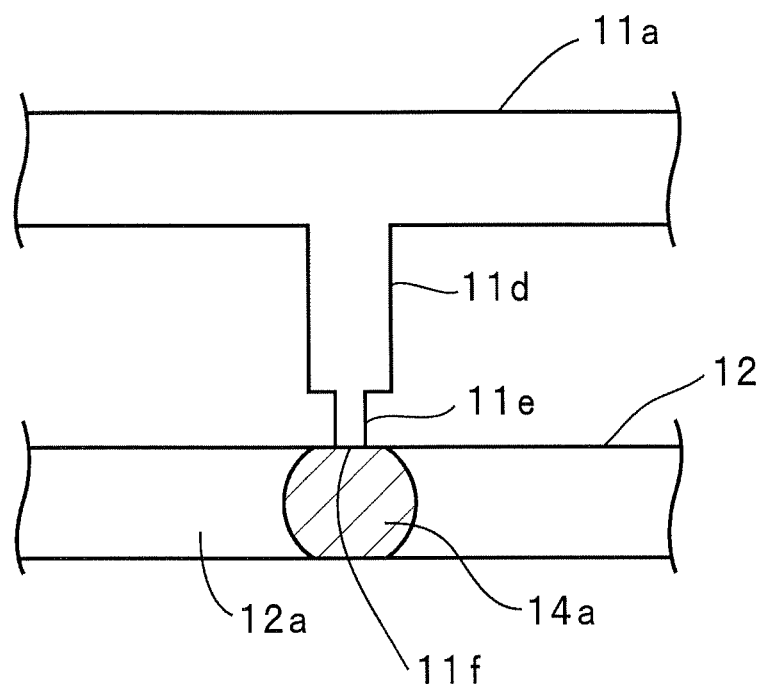
FIG. 7 is a partial cross-sectional enlarged plan view for describing a process of measuring a fixed amount of the first micro-droplet for the first measuring section, in embodiment illustrated in FIG. 1.

The configuration where a fixed amount of the micro-droplet is measured in the first measuring section 11d will be described with reference to FIG. 5 to FIG. 7.

The micro-droplet is injected in from the liquid supply hole 11c. In this case, the interior of the first micro-channel 11a is released to the atmospheric air. That is, the gas supply hole 11b is opened to the atmospheric air. In injection of the micro-droplet from the liquid supply hole 11c, the micro-droplet is injected with pressure from the liquid injection hole 11c using a micro syringe etc. As a result, the micro-droplet 14 is sent in the first micro-channel 11a, and it fills the first measuring section 11d consisting of branched micro-channel, as illustrated in FIG. 5.

In this embodiment, provided is a micro-channel for connection 11e having a diameter smaller than the diameter of the micro-channel that configures the first measuring section 11, on the top end side of the first measuring section 11d. Since the diameter of the micro-channel for connection 11e is very small, the micro-droplet 14 cannot flow through the micro-channel for connection 11e with a pressure as the applied injection pressure affected by influence of the surface tension, resulting in suspension of movement at the inlet or exit of the micro-channel for connection.

Next, a gas is supplied to the first micro-channel 11a from the gas supply hole 11b. In this case, the liquid supply hole 11c is released to atmospheric air. As a result, the first micro-droplet 14a will remain as a fixed amount of the micro-droplet in the first measuring section 11d as illustrated in FIG. 6. In this way, the second flow path 12 side is preferably closed and not released to the atmospheric air, when supplying the gas in order to make the micro-droplet 14a remain in the first measuring section 11d. By the way, when the micro-chancel for connection 11e is fine enough, and the capillary tube reaction force works in the micro-channel for connection 11e, the second micro-channel 12 side may be sealed.

Next, a part at the side of the liquid supply hole 11c of the first micro-channel 11a is closed by a below-mentioned valve of the flow path opening and closing mechanism, etc., and in this condition, a gas is supplied to the first micro-channel 11a from the gas supply hole 11b. As a result, the first micro-droplet 14a that has been measured in the first measuring section 11d is exhausted into the second micro-channel 12 as illustrated in FIG. 7.

Since the first micro-droplet 14a that has been measured in the first measuring section 11d has the same volume as the capacity of the first measuring section 11d, this embodiment can allow reliable exhaust of a fixed amount of the first micro-droplet 14a into the second micro-channel 12.

The above-described flow path opening and closing mechanism may be provided with a suitable valve enabling switching of a part of the micro-channel between an opened state and a closed state. As such a valve, a structure may be used wherein a stopper allowing transfer between a state of a flow path made small, and a state of a flow path made open is connected to a drive element, such as a solenoid valve and a piezoelectric element.

Figure 4:
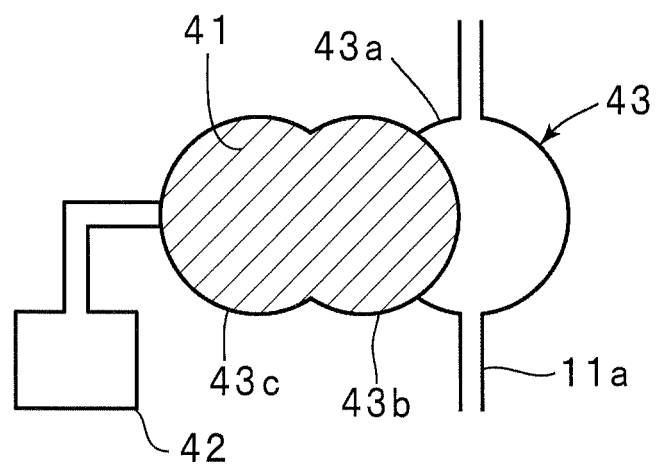
FIGS. 4(a) and (b) are each schematic plan view for describing an example of a flow path switching device, and (c) is a schematic plan view illustrating modification of the flow path switching device.
Figure 4:
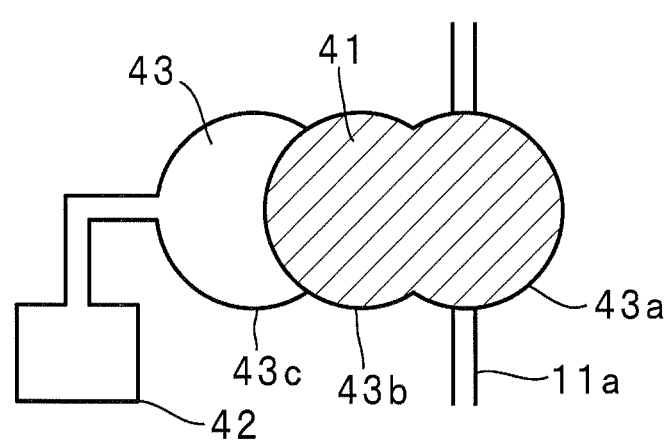

In addition, a flow path opening and closing mechanism using a combination of a viscoelastic stopper 41, and a drive source for stopper 42 by gas or liquid may be used as illustrated in FIG. 4(a). Here, the viscoelastic stopper 41 may be provided by a suitable material having elasticity and allowing movement by increase of pressure in the flow path, such as elastomers or gels. When the micro-droplet to be sent is an aqueous solution, a viscoelastic material that does not have water solubility is suitably used, and when it is an organic solvent, a viscoelastic material that does not have solubility with respect to organic solvents is preferably used.

As illustrated in FIG. 4(a), a stopper passage section 43 allowing retraction of the viscoelastic stopper 41 is formed in a part of the micro-channel 11a to be opened and closed. The stopper passage section 43, in this embodiment, has a shape wherein three round shapes arranged in a direction intersecting perpendicular to a direction of extension of the micro-channel 11a, the three round shapes partially overlapping with each other. One circular section 43a out of the three circular sections 43a to 43c is provided in the course of the above-described first micro-channel 11a, and the remaining circular sections 43b and 43c are disposed in the side of the first micro-channel 11a. In FIG. 4(a), the viscoelastic stopper 41 is disposed in the second and the third circular sections 43b and 43c, and thus the micro-channel 11a is set in an open state in this condition.

As illustrated in FIG. 4(b), a gas is generated in the drive source 42 and thereby the viscoelastic stopper 41 is shifted by the pressure to the side. As a result, the viscoelastic stopper 41 shifts to the first and the second circular section 43a, and 43b side, and contacts the interior surface of the first circular section 43a. Therefore, the first micro-channel 11a is transferred into closed state.

Such a mechanism enables switching of the first micro-channel 11a from the open state to the closed state. Incidentally, when the mechanism is needed to return to the open state again, for example, a second drive source may be connected to the first circular section 43a, a gas is again supplied from the second drive source side, and the viscoelastic stopper 41 may just be made shift to the state of FIG. 4(a).

Alternatively, a gas-suction source may be connected instead of the gas drive source 42 in the condition illustrated in FIG. 4(b), and thereby the viscoelastic stopper 41 may be returned by suction to the open state illustrated in FIG. 4(a).

Returning to FIG. 3. The above described flow path opening and closing mechanism is provided in the course of the first micro-channel 11a, and thereby a fixed amount of the first micro-droplet 14a may be measured into the first measuring section 11d in the above described manner, and furthermore may be exhausted out to second micro-channel 12 as described above, using the pressure of the gas supplied from the gas supply hole 11.

Also in the third micro-channel 13a, the second micro-droplet corresponding to the capacity of the second measuring section 13d ma be measured into the second measuring section 13d, and may be exhausted out to the second micro-channel 12 in the same manner as described above.

Figure 8:
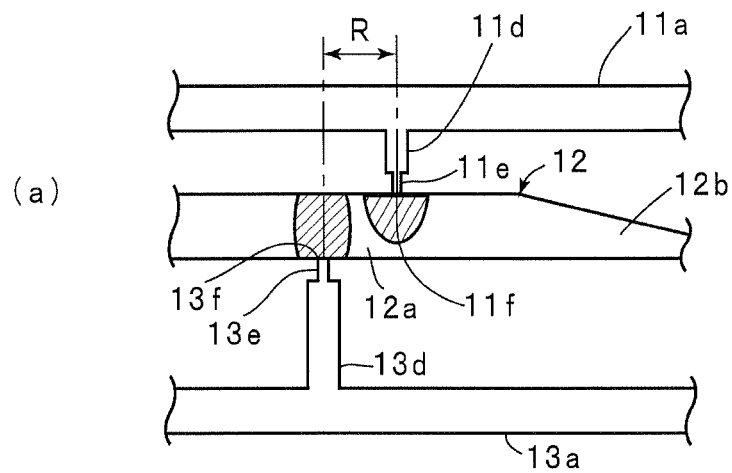
FIG. 8 is a schematic partial cross-sectional plan view where micro-droplets are exhausted from the first and the second measuring sections to the second micro-channel, respectively, in the first embodiment.
Figure 8:
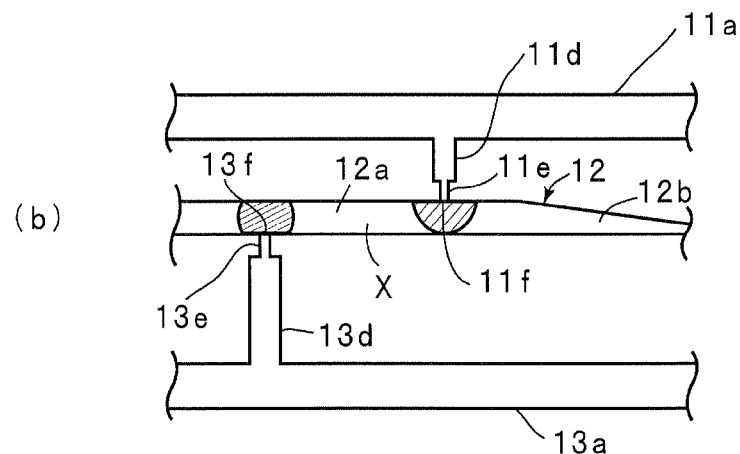
Figure 8:
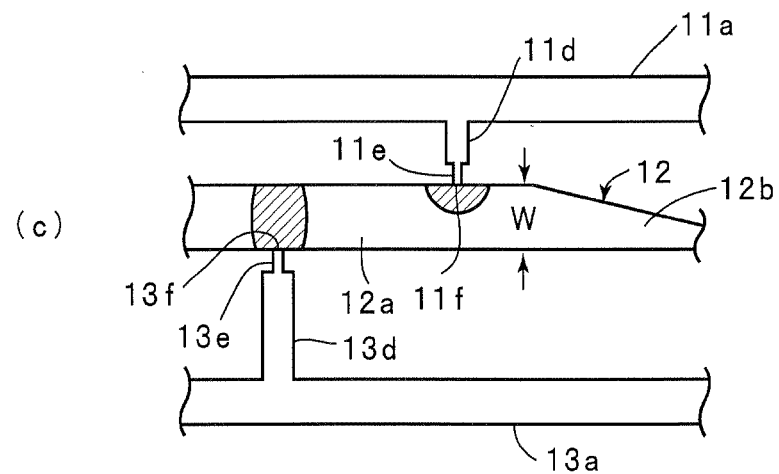

Incidentally, the second measuring section 13d is formed so that it may have a capacity corresponding to the volume of the second micro-droplet. In this embodiment as illustrated in the schematic partial enlarged plan view in FIG. 8, the second measuring section 13d also has a micro-channel for connection 13e, at the top end thereof, having a width narrower than the fineness of the micro-channel that configures the second measuring section 13d.

Disposing of the above-described micro-channels for connection 11e and 13e can ensure suppression of leakage of the micro-droplet to the side of second micro-channel 12 prior to exhaust of the first and second micro-droplet to the second micro-channel 12. When the micro-droplet is an aqueous solution and the wall surface of the micro-channel for connection is hydrophilic, the micro-droplet stops at the exit of the micro-channel. In addition, when the micro-droplet is an aqueous solution and the wall surface of the micro-channel for connection is hydrophobic, the micro-droplet stops at the inlet of the micro-channel. Furthermore, when the micro-droplet is an oily solution and the wall surface of the micro-channel for connection is hydrophilic, the micro-droplet stops at the inlet of the micro-channel, and when the micro-droplet is an oily solution and the wall surface of the micro-channel for connection is hydrophobic, the micro-droplet stops at the exit of the micro-channel.

Here, in place of using the above-described micro-channel for connection 11e and 13e, leakage of the first micro-droplet 14a and second micro-droplet from the opening of the above-described second micro-channel 12 may be suppressed by providing lower wettability to the wall surface of the opening in the second flow path 12 of the first, and the second measuring sections 11d and 13d. Here, known partial water repellent finishing methods may be adopted as a measure for providing lower wettability.

In this embodiment, the opening 13f can serve as the third outlet port (the outlet port of the third micro-channel 13a) of the mixing unit(s) (see, for example, each of the first, ascend, and third mixing units 11, 21, and 31 in the embodiment shown in FIG. 1), on the second micro-channel 12 of the second measuring section 13d, and the opening 11f can serve as the first outlet port (the outlet port of the first micro-channel 11a in the first mixing unit 11 and optionally the outlet port of the first micro-channel 11d in the second and third mixing units 21 and 31) of the mixing unit(s) (see, for example, each of the first, second, and third mixing units 11, 21, and 31 in this embodiment shown in FIG. 1), on the second micro-channel 12 of the first measuring section 11d are disposed at different positions with each other in a direction of flow of the micro-droplet in the second micro-channel 12. That is, the opening 13f and the opening 11f are separated with each other with a distance R in FIG. 8 therebetween. Here, the distance R represents a center-to-center distance of the opening 13f and the opening 11f.

The opening 11f of the first measuring section 11d and the opening 13f of the second measuring section 13d may be disposed so as to face with each other in the second micro-channel 12. However, it is very difficult that they both are disposed facing with each other, and that the first and the second micro-droplets are exhausted from the first and second measuring sections 11d and 13d, respectively, to the second micro-channel 12 at almost the same timing. Even with concurrent driving of the flow path opening and closing mechanism etc., the timing of exhaust of the first and the second micro-droplet actually may slightly shift in timing.

Only a slight lag of timings of exhaust between the first and the second micro-droplets makes one of the micro-droplet attach to the opening part of the measuring section for another micro-droplet, and causes leakage of the micro-droplet having been measured in the measuring section for another micro-droplet, resulting in difficulty of mixing of the first and the second micro-droplet with accurate volume ratio.

Alternatively, in this embodiment, the opening 11f of the first measuring section 11d and the opening 13f of second measuring section 13d are separated by the above-described distance R. Accordingly, when the exhausting timing of the first micro-droplet 14a from the first measuring section 11d is different from the timing of exhausting of the second micro-droplet from the second measuring section 13d. For example, when the first micro-droplet 14a is exhausted in advance in the downstream, the first micro-droplet 14a will not easily attach to the opening 13f of the second measuring section 13d, hardly causing leakage of the micro-droplet that has been measured by the second measuring section 13d. That is, the above-described distance R is desirably designed as a distance of sufficient distance to avoid contact of the exhausted micro-droplet to the opening of measuring section in another side.

Whereas, as shown in FIG. 8(b) schematically, the above-described excessively large distance R extremely separates the drop of the first micro-droplet 14a exhausted from the first measuring section 11d, and the drop of the second micro-droplet 13b exhausted from the second measuring section 13d, resulting in formation of an air layer X therebetween. Accordingly, there will be a possibility that involvement of the air bubble between the drops cannot easily provide sufficient mixing between the micro-droplet 14a and the micro-droplet 14b.

Therefore, as illustrated in FIG. 8(a), the distance R is desirably small to an extent avoiding involvement of the air bubble between the first micro-droplet 14a and the second micro-droplet 14b.

However, even when the above-described distance R is large, a width W large enough in the merging section 12a of the second micro-channel 12 can also avoid involvement of air. That is, as illustrated in FIG. 8(c), it is desirable for the width W of the second micro-channel 12 in the merging section 12a to be larger than the dimension of the exhausted first micro-droplet 14a in the above-described width W direction so as to avoid contact of the first micro-droplet 14a to the inner wall of the second micro-channel located in the opposite side with respect to the opening 14e in the stage of completion of exhaust of the first micro-droplet 14a. In this case, even when an air layer is formed between the first micro-droplet 14a and the second micro-droplet 14b, air will pass between the first micro-droplet 14a and the inner wall of the flow path of the opposite side in liquid sending of the second micro-droplet 14b, and therefore the air can escape, hardly causing involvement of air.

Figure 9:
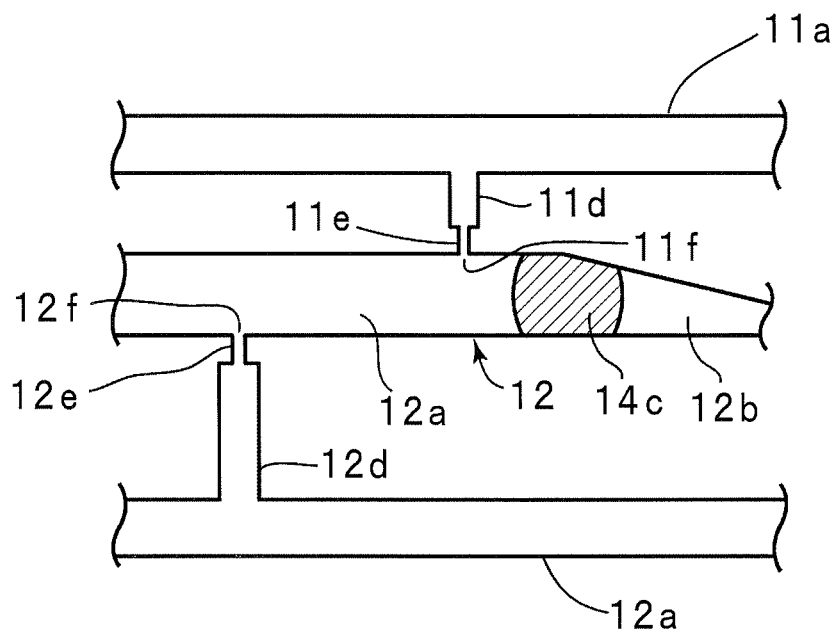
FIG. 9 is a partial cross-sectional plan view illustrating a condition where a micro-droplet passes through a mixing section in the first embodiment.

Returning to FIG. 3 here. The supply of the gas from the gas supply hole 12d provided in the upstream side of the second micro-channel 12 merges the above-described first and the second micro-droplets 14a and 14b, and the liquid in the merged condition will flow in the downstream side. And, as illustrated in FIG. 9, the planar shape of both sides of the micro-channel in a width direction of the above-described second micro-channel 12b is designed to be asymmetric in the mixing section 12b, leading to mixing of the mixed droplet 14c. That is, the above-described asymmetric shape generates swirl in the mixed droplet 14c, and thus agitates the mixed droplet 14c, resulting in reliable mixing. Here, a tapered slope is formed so that one of the inner wall of the second micro-channel 12 may approach the inner wall of the opposite side as advancing in a downstream side. Accordingly, swirls will be caused in the above-described mixed droplet 14, and agitation action sufficiently mixes the first and the second micro-droplet.

Accordingly, this embodiment can eliminate the necessity for disposing of a large mixing chamber in the mixing unit 11, or in the downstream of the mixing unit 11. Elimination of the necessity for the mixing chamber provides advantage in integration, processing within a shorter period of time, and interconnection of the microfluidic devices.

In this embodiment, the mixed droplet sufficiently mixed is exhausted from the exhausting section 12c provided in the downstream of the mixing section 12b. And in this embodiment, the mixed droplet 14c exhausted from the exhausting section 12c of the first mixing unit 11 will be supplied to the first measuring section of the second mixing unit 21 from the first inlet port mentioned later. That is, the mixed result of the first mixing unit 11 is to be used in the second mixing unit 21. A multi-stage configuration may be obtained by direct connection of the second mixing unit 21 to the first mixing unit 11 for mixing the micro-droplet, and thereby a micro-droplet having a higher dilution ratio as compared with the dilution ratio in a single-step configuration may be obtained.

Figure 10:
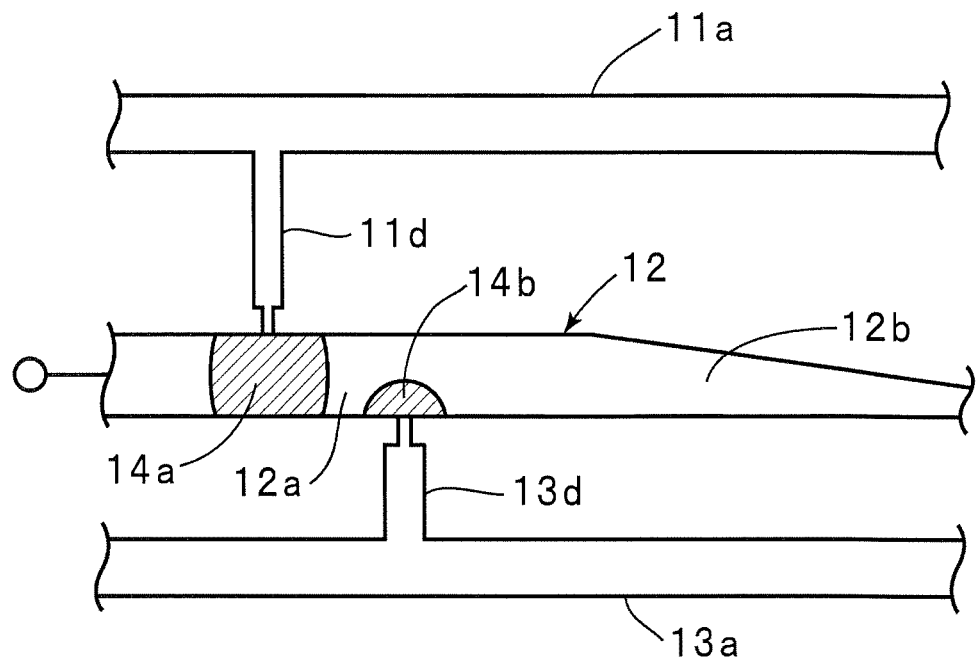
FIG. 10 is a schematic plan view for describing the physical relationship of the first and the second measuring sections in modification of the first embodiment.

Incidentally, in the above-described embodiment, an opening, having a larger volume as compared with the volume of the first measuring section 11d, of the second measuring section 13d was disposed in the upstream in the merging section 12a. Alternatively, the first measuring section 11d may be disposed so as to have an opening to the merging section 12a in the upstream of the second measuring section 13d as in a variation illustrated in FIG. 10. In this modification, the volume of the first measuring section 11d in the upstream may just be set to be larger than the volume of the second measuring section 12d in the downstream.

Figure 11:
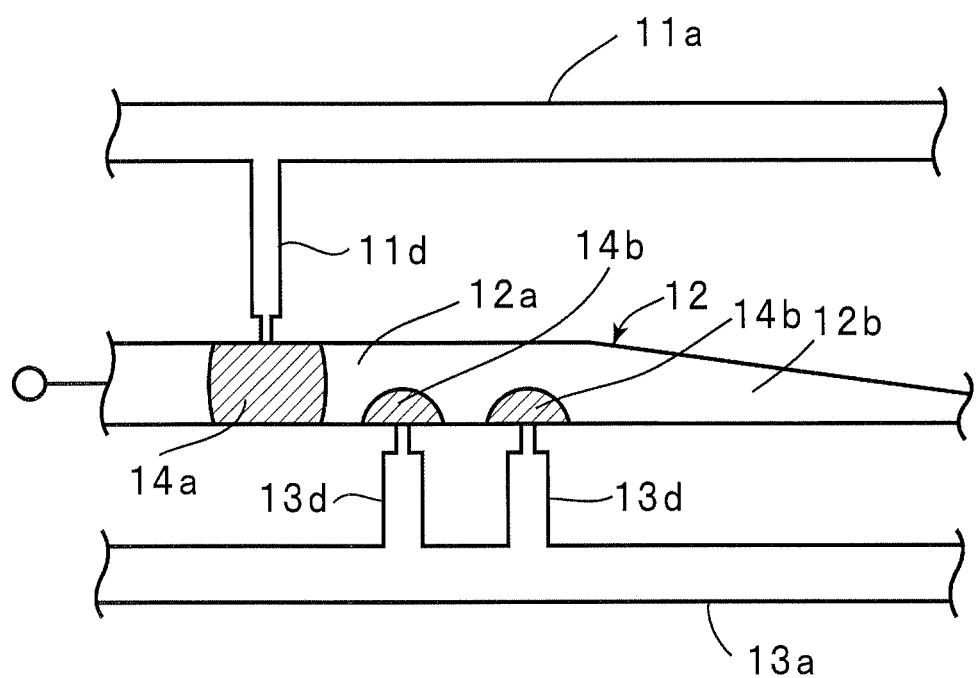
FIG. 11 is a schematic plan view illustrating a modification that has a plurality of second measuring sections, in order to obtain different blending ratios in the merging section.

Alternatively, a plurality of the second measuring sections 13d and 13d may be connected to merging section 12a as in an other modification illustrated in FIG. 11. In this case, the mixing ratio of the second micro-droplet may be raised.

Figure 12:
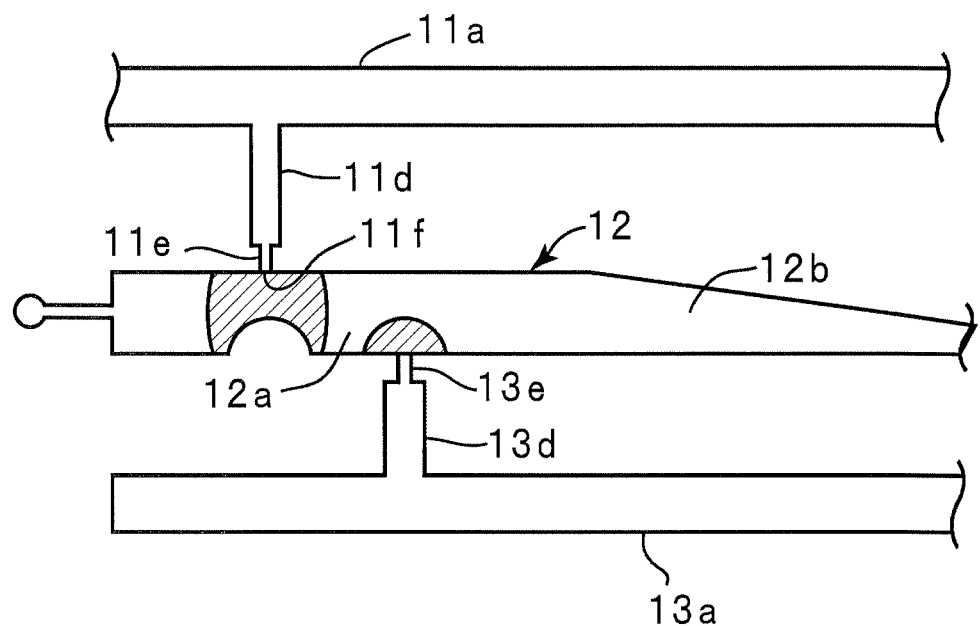
FIG. 12(a) is a schematic plan view illustrating other modification wherein the shape of the second micro-channel is deformed, and thereby the mixing percentage in the merging section is varied, and (b) is a schematic partial cross-sectional plan view for describing a modification of the shape of the merging section.
Figure 12:
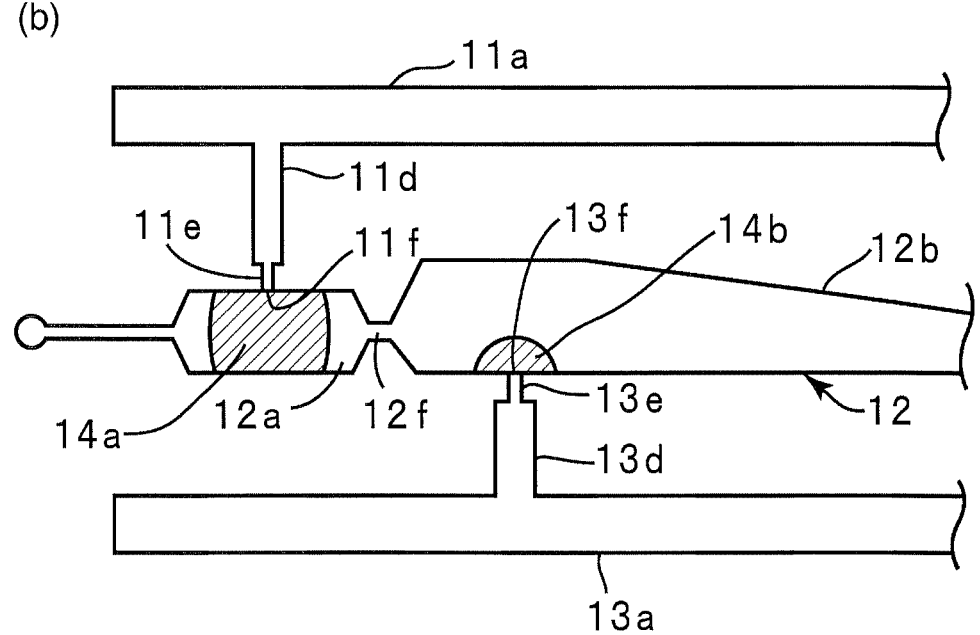

In addition, as in a variation illustrated in FIG. 12, the wall surface in the opposite side of the opening 11f in which the first measuring section 11d has the opening may be made to project in the opening 11f side in the second micro-channel 12, and thereby the width of the second micro-channel 12 in a portion where the first micro-droplet 14a is to be exhausted may be reduced. In this case, since the first micro-droplet reaches the wall in the opposite side of the merging section even when the first measuring section has a smaller volume, operational stability may be guaranteed even in case of a smaller volume ratio between the first measuring section and the second measuring section. For example, mixing in a ratio of 1 to 1 of the first and the second micro-droplets may be obtained in the merging section 12a Furthermore, as in a variation illustrated in FIG. 12(b), a fine width part 12f having a width relatively narrower than the remaining portion may be provided in the merging section 12a in the halfway in the direction of flow of the micro-droplet in the second micro-channel 12. Here, the merging section 12a has the fine width part 12f in the center in the direction of the flow of the micro-droplet. Thus, the opening 11f of the first measuring section 11d has an opening in the upstream of the fine width part 12f, and the opening 13f of the second measuring section 13d has an opening in the downstream of the fine width part 12f.

Also here, in the downstream of fine width part 12f, when the width of the second micro-channel 12 is set larger than the diameter of the drop of the micro-droplet exhausted out from the second measuring section 13d, the first and the second micro-droplets can merge in the merging section 12a while preventing involvement of air. That is, air located between the first micro-droplet 14a and the second micro-droplet 14b will escape in the downstream side in movement downward of the first micro-droplet 14a exhausted in the upstream by a gas pressure from the gas supply hole 12d. Therefore, the first and the second micro-droplets 14a and 14b may merge without involvement of air bubbles. However, it is necessary for a drop after merging of the first micro-droplet and the second micro-droplet to be a drop that can fill the width of the second micro-channel 12.

The microfluidic device of the present invention has at least a configuration having the first and the second mixing units connected together. In this case the mixing unit has the first to third micro-channels as described above, and moreover the second micro-channel has, from the upstream side, the merging section, the mixing section, and the exhausting section. Such first and second mixing units may be connected together in various forms.

Modifications of connection configuration of the second mixing unit to the first mixing unit will be described, respectively with reference to FIG. 13 to FIG. 17.

Figure 13:
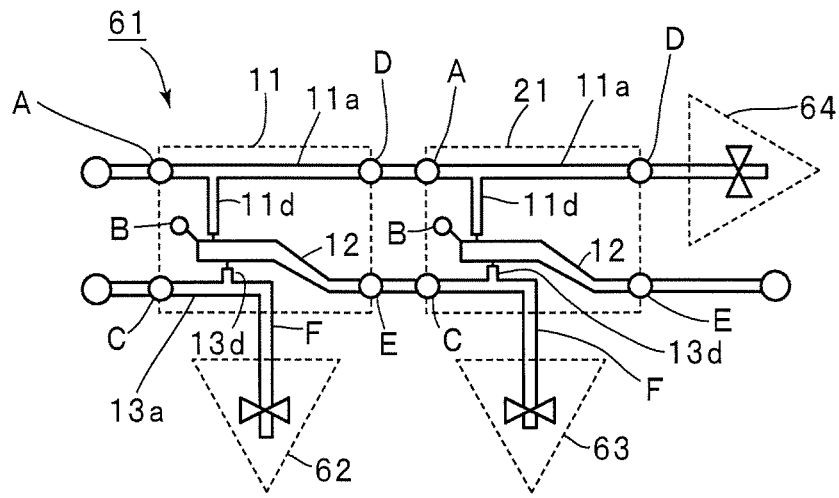
FIG. 13 is a plan view schematically illustrating an other modification of a micro-channel structure to which the first and the second mixing units are connected.

FIG. 13 is a plan view schematically illustrating a configuration wherein the first and the second mixing units are connected using a mixed result in the first mixing unit, in the same manner as in the above-described embodiment illustrated in FIG. 1. Here, the second mixing unit 21 is connected in the subsequent stage of the first mixing unit 11 as in the above-described embodiment. In figures of micro-channel structures after FIG. 13, the mixing unit, the flow path opening, and closing mechanism, etc. will suitably be illustrated as a block enclosed with broken line.

In the micro-channel structure 61 illustrated in FIG. 13, the second mixing unit 21 is connected in the downstream of the first mixing unit 11 as in the above-described embodiments. Here, the first mixing unit 11 may be represented as a configuration having the first to third inlet ports A to C, and the first to third outlet ports D to F. That is, the first micro-channel 11a is connected between the first inlet port A and the first outlet port D. One end of the first measuring section 11d is connected to the first micro-channel 11a, and an other end of the first measuring section 11a is connected to the second micro-channel 12. The second micro-channel 12 is connected between the second inlet port B and the second outlet port E. The above-described third micro-channel 13 is connected between the third inlet port C and the third outlet port F. The second outlet port E is connected to the exhausting section, and this is equivalent to a portion that exhausts the mixed droplet outside. Furthermore, the third outlet port F is connected to the flow path opening and closing mechanism 62.

The first inlet port A of the second mixing unit 21 is connected to the first outlet port D of the first mixing unit 11, and the second inlet port B of the second mixing unit 21 is connected to the gas supply hole. The third inlet port C is connected to the second outlet port E of the above-described first mixing unit 11. Accordingly, the mixed droplet in the first mixing unit 11 is supplied from the third inlet port C of the second mixing unit 21, and then the micro-droplet is measured by the second measuring section 13d of the second mixing unit 11.

Accordingly, a result mixed in the first mixing unit 11 will be used in the second mixing unit 21. Therefore, dilution at a higher magnification may be obtained by the above described connection of the first and the second mixing units 11 and 21 in the case of a configuration that supplies a diluting solution from the first measuring section 11d.

Furthermore, the flow path opening and closing mechanism 63 is connected also to the third outlet port of the above-described second mixing unit 21. Similarly, the flow path opening and closing mechanism 64 is also connected with respect to the first outlet port D of the second mixing unit 21. A micro-droplet diluted at a high magnification is exhausted from the second outlet port E, and is sent to the test section and the reaction section provided in the subsequent stage.

Figure 14:
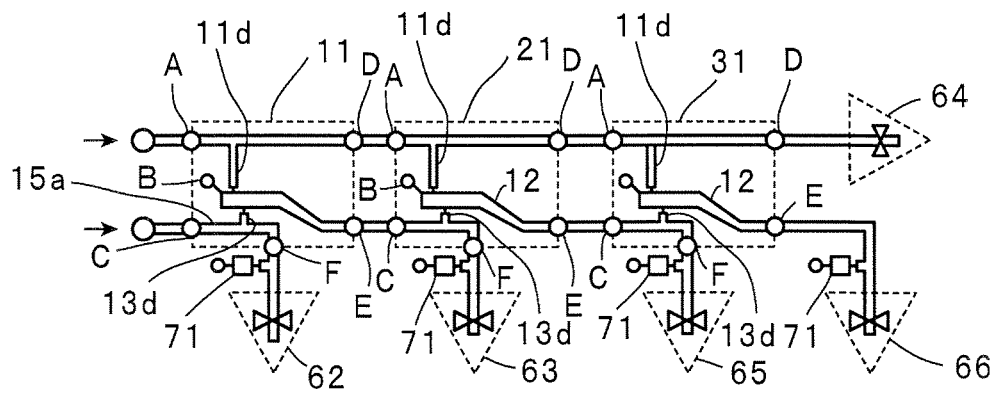
FIG. 14 is a schematic plan view illustrating another modification of a micro-channel structure of a microfluidic device according to the present invention.

FIG. 14 is a plan view schematically illustrating a configuration wherein the third mixing unit 31 is further connected in the downstream of the above-described first and second mixing units 11 and 21. Thus, one or more mixing units 31 may further be connected in the downstream of the first and the second mixing units 11 and 21. Furthermore, each of the third outlet ports F of the first to third mixing units 11, 21, and 31 are connected to the flow path opening and closing mechanisms 62, 63, and 65, respectively, the branching channel is formed between the outlet port F and flew path opening and closing mechanism, and then the branching channel is connected to the storing chamber 71 in the configuration illustrated in FIG. 14. A reaction cell may be provided instead of the storing chamber 71.

Accordingly, micro-droplets having the dilution ratios respectively different from each other will be prepared in the storing chambers 71, 71, and 71 connected to each of the third outlet ports F of the first to third mixing units. Furthermore, the flow path opening and closing mechanism 66 and the storing chamber 71 are similarly connected also to the second outlet port E connected to the exhausting section of the third mixing unit 31, and thus a micro-droplet having different dilution ratio is to be prepared also in the storing chamber 71.

Figure 15:
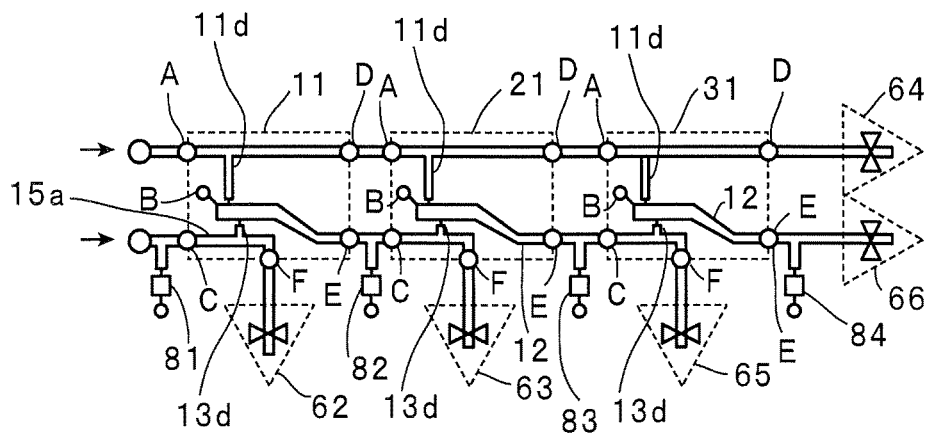
FIG. 15 is a schematic plan view illustrating a modification of a micro-channel structure illustrated in FIG. 14.

FIG. 15 is a schematic plan view illustrating a modification of the micro-channel structure illustrated in FIG. 14. In FIG. 14, the above-described storing chamber 71 was connected between the third outlet ports F of the first to the third mixing units 11, 21, and 31, and the flow path opening and closing mechanism, and here in FIG. 15, the storing chamber 31 is connected to the preceding stage of the third inlet port C of the first mixing unit, and the storing chambers 82 to 84 are connected, respectively to the downstream of the second outlet port E of the first to the third mixing units 11, 21, and 31. In this storing chambers 82 to 84, mixed results in the mixing units 11, 21, and 31 in each stage will be measured.

The trace amount of liquid dilution method of the present invention may be performed using the microfluidic device having the micro-channel structure illustrated in FIG. 14 and FIG. 15. For example, in the micro-channel structure illustrated in FIG. 14, a diluting solution is measured as the first micro-droplet in the first measuring section 11d of the first mixing unit 11. On the other hand, a sample to be diluted as the second micro-droplet is measured in the second measuring section 13d. This sample and the diluting solution are mixed in the first mixing unit 11, and then the mixture is exhausted from the exhausting section of the second micro-channel 12 of the first mixing unit 11 through the second outlet port E. Then, in the second mixing unit 21, in the same manner as in case of the first mixing unit 11, a diluting solution is measured in the first measuring section 11d as the first micro-droplet in the first measuring section 11d.

On the other hand, in the second measuring section 13d, the above-described diluted solution of sample that is the mixed result of the first mixing unit 11, that is, a diluted solution of sample as the first mixed droplet exhausted from the outlet port E are measured. In FIG. 14, the storing chamber 71 is disposed to the third outlet port F of the second mixing unit 21, and the above-described first mixed droplet, that is, the first diluted solution of sample, is stored in the storing chamber 71. Furthermore, the first diluted solution of sample and diluting solution are mixed in the second mixing unit 21, a diluted solution of sample as the obtained second mixing micro-droplet is exhausted from cutlet port E of the second mixing unit 21, and then is supplied to the chamber 71 connected through the outlet port F of the third mixing unit 31. Accordingly, the first and the second diluted solutions of sample having concentrations different from each other will be supplied in each chamber 71 or 71 connected to the side of the second mixing unit 21 and the third mixing unit 31.

In the micro-channel structure illustrated in FIG. 15, the first diluted solution of sample is provided in the storing chamber 82 connected between the first mixing unit 11 and the second mixing unit 21, and the second diluted solution of sample is provided into the storing chamber 83 connected between the second mixing unit 21 and the third mixing unit 31.

In this way, the trace amount of liquid dilution method of the present invention is carried out using the micro-channel structure illustrated in FIG. 14 and FIG. 15, and a plurality of diluted solutions of sample having concentrations different from each other may be prepared. In FIG. 14 and FIG. 15, the third mixing unit 31 is further connected as described above, and thereby three kinds of diluted solutions of samples having concentrations different from each other may be provided.

Furthermore, still more mixing units may be connected to the next step of the first and the second mixing units as in Examples mentioned later. In this case, when n−2 of mixing units (n is natural number) are connected to the downstream of the first and the second mixing units, n kinds of diluted solutions of sample having concentrations different from each other may be prepared.

Conversely in case of FIG. 14 and FIG. 15, a sample may be measured in the first measuring section and a diluting solution may be measured in the second measuring section.

Figure 16:
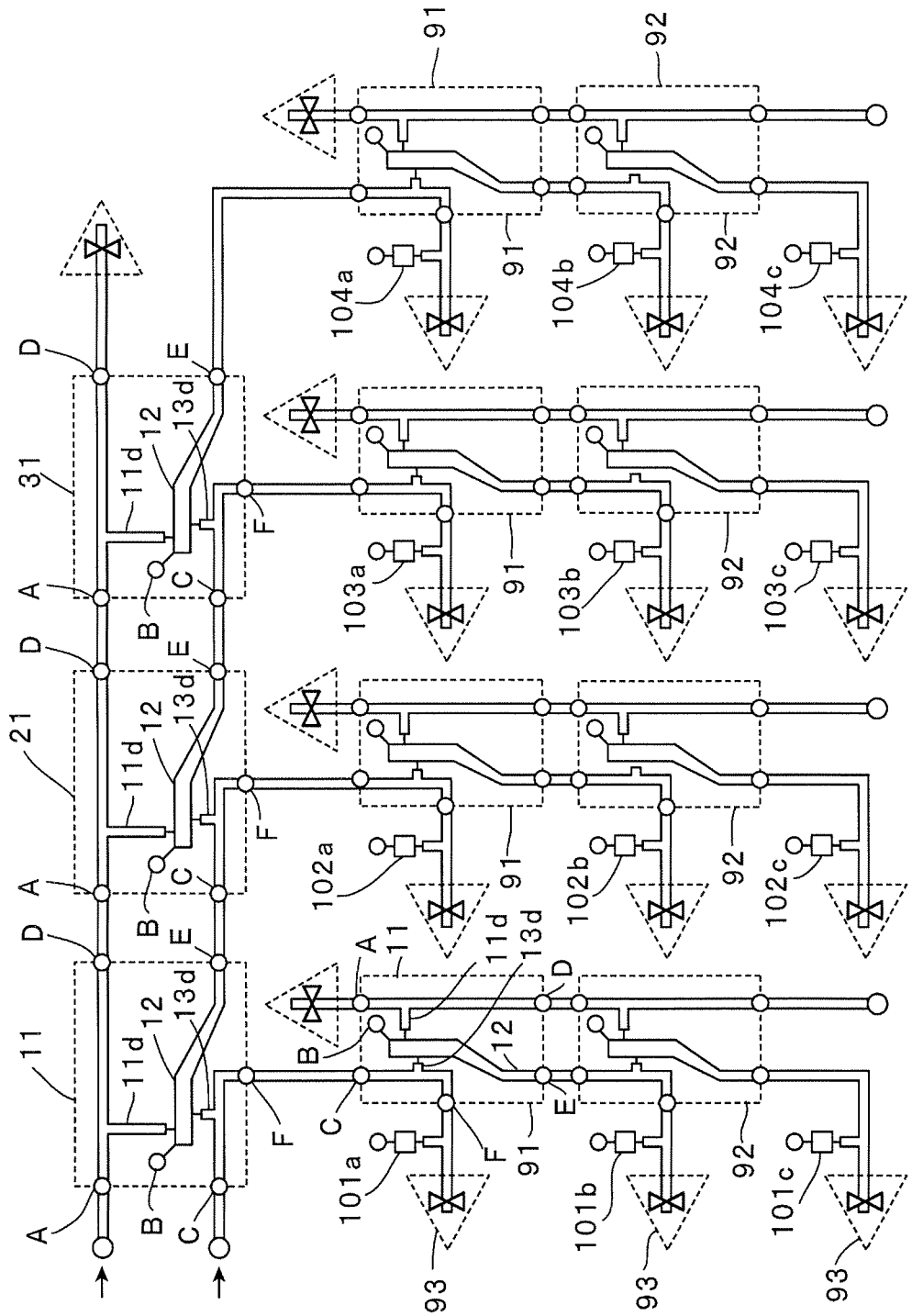
FIG. 16 is a schematic plan view illustrating another modification of a micro-channel structure of a microfluidic device of the present invention, and illustrating a modification wherein a large numbers of mixing units are disposed in a matrix.

Furthermore, FIG. 16 is a schematic plan view illustrating a micro-channel structure wherein still more mixing units are connected in a matrix form. Here, the first to the third mixing units 11, 21, and 31 are configured in the same manner as in the micro-channel structure illustrated in FIG. 14. However, a flow path opening and closing mechanism and a storing chamber are connected to each of the third outlet ports F of each of the mixing units 11, 21, and 31, and furthermore a micro-channel structure wherein the fourth and fifth mixing units are further connected in series is connected to the third outlet port. That is, when the first to the third mixing units 11, 12, and 13 are defined as the direction of line, the fourth and fifth mixing units 91 and 92 are connected to each of the mixing units 11, 21, and 31 in a column direction of a matrix consisting of lines and columns. The connection configuration of the fourth and fifth mixing units is the same as that of the first and the second mixing units.

That is, the fourth and fifth mixing units 91 and 92 are connected to satisfy the same connecting relationship as the connecting relationship between the first and the second mixing units 11 and 21 so that the mixed result in the fourth mixing unit 91 may be used in the fifth mixing unit 92. And the flow path opening and closing mechanism 93 and the storing chamber are connected to the second outlet port E of the fifth mixing unit. Furthermore, the flow path opening and closing mechanism 93 and the storing chamber are connected similarly to each of the third outlet ports F and F of the fourth and fifth mixing units 91 and 92.

Accordingly, in the micro-channel structure illustrated in FIG. 16, when the first measuring section 11d in each mixing unit and the second measuring section 13d is assumed to exhaust the same amount of the micro-droplet, the dilution ratios in a large number of the storing chambers in a matrix form will respectively be given as follows. Incidentally, the dilution ratio is represented with a proportion of the undiluted solution in the mixed droplet, for example, when an undiluted solution is measured in the second measuring section 13d of the first mixing unit 11, and dilution is performed in each following mixing unit. For example, since the original undiluted solution is prepared in the storing chamber 101a, 1/1 is given for the dilution ratio, and 1/3 will be given for the dilution ratio of the undiluted solution in the storing chamber 101b. That is, in the storing chambers 101a to 101c positioned in the side of the fourth and fifth mixing units 91 and 92 connected to the first mixing unit 11, the dilution ratio will give 1/1, 1/3, and $1/3^2$. Similarly, the dilution ratio in the storing chambers 102a to 102c disposed in the side of the fourth and fifth mixing units connected to the second mixing unit 21 will give $1/3^3$, $1/3^4$, and $1/3^5$, respectively. Furthermore, the dilution ratio in the storing chambers 103a to 103c disposed in the side of the fourth and fifth mixing units connected under the third mixing unit 31 will give $1/3^6$, $1/3^7$, and $1/3^8$.

In addition, similarly the dilution ratio in the storing chambers 104a to 104c disposed in the side of the fourth and fifth mixing units connected to the second outlet port of the third mixing unit 31 will give $1/3^9$, $1/3^{10}$, and $1/3^{11}$. Accordingly, the microfluidic device that can automatically prepare a series of dilution series in a short period of time may be obtained by disposing the storing chambers 101a to 104c in a matrix form as described above. Incidentally, it is also obvious that selection of mixture ratio in each of the mixing units can also give dilution series different from the above described examples. For example, dilution series giving $1/2^n$ may also be obtained by replacing the above-described examples to a mixing unit allowing mixing by 1 to 1 as illustrated in FIG. 13. Thus, it becomes possible to provide easily micro-droplets giving various kinds of dilution ratios.

Figure 17:
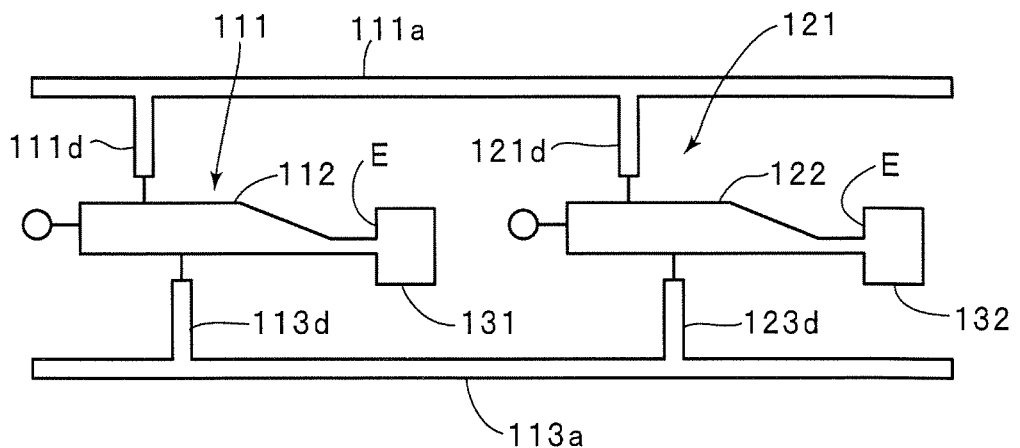
FIG. 17 is a schematic plan view illustrating a still another modification of a micro-channel structure of a microfluidic device of the present invention.

FIG. 17 is a schematic plan view illustrating a still other modification of the micro-channel structure in the microfluidic device of the present invention. In the above-described embodiments and modifications, the first and the second mixing unit were connected so that the mixed result in the first mixing unit might be used, but the first mixing unit 111 and the second mixing unit 121 may be connected in parallel as illustrated in FIG. 17. Here, the first measuring section 111d of the first mixing unit 111, and the first measuring section 121d of the second mixing unit 121 are connected in common by the first micro-channel 111a.

Similarly, the second measuring section 113d of the first mixing unit 121, and the second measuring section 123d of the second mixing unit 121 are also connected in common by third micro-channel 113a. Then, the storing chambers 131, 132 are connected to the exhausting section provided in the downstream of each of the micro-channels 112, 122 of the first and the second mixing units 111, 121, respectively. Accordingly, the micro-droplets having the same dilution ratios with each other may be obtained from each of the storing chambers 131,132 connected to the first and the second mixing units 111, 121.

In other words, the first and the third outlet ports D and F of the first mixing unit are connected to the first and the third inlet ports A and C of the second mixing unit 121, respectively, and the micro-droplets having the same dilution ratio are configured to be exhausted from the second outlet ports E and E of each mixing units 111, 121.

In the present invention, in addition, a parallel connection that gives the micro-droplet having the same dilution ratio illustrated in FIG. 17, and a connection configuration as illustrated in the above-described embodiments and modifications may be used together in combination.

Figure 18:
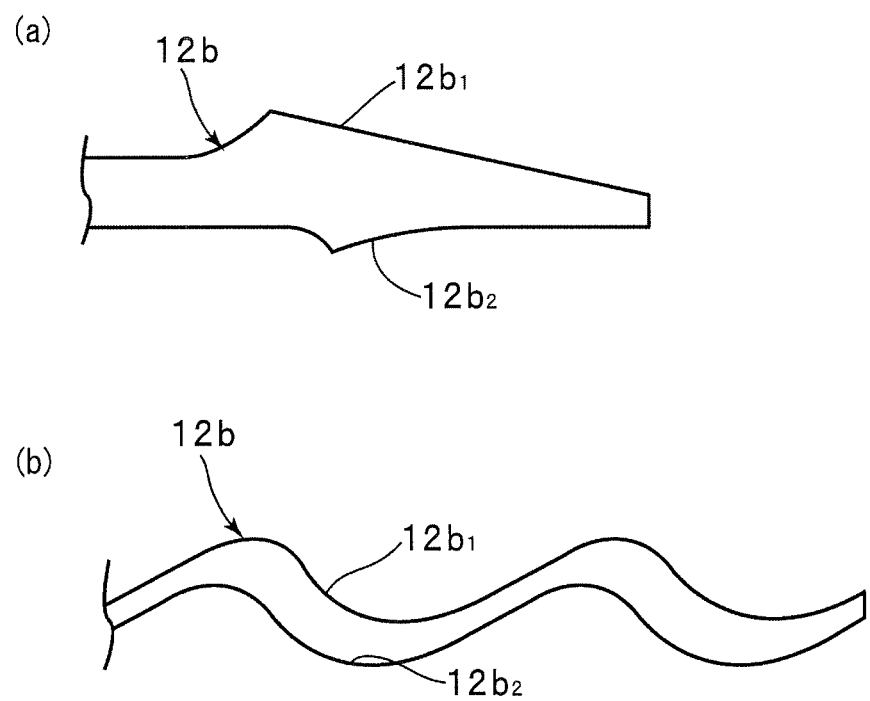
FIGS. 18(a) and (b) are each a plan view illustrating a modification of a shape of a mixing section.

Incidentally in the above-described embodiment, the wall surface positioned in both sides in a width direction may be asymmetric in the second micro-channel in the mixing section, and a tapered slope is formed so that one of the wall may approach the other wall on the opposite side as advancing in a downstream side. The shape of the mixing section is not limited to such shapes. For example, as illustrated in FIG. 18(a), in the mixing section 12b, one wall surface $12b_1$ may be formed once to be widened as it advances in the downstream, then advances linearly so that the wall surface $12b_2$ on the opposite side may be approached. Furthermore, the wall surface $12b_2$ in another side may be formed also to be widened outside in a portion different from the wall surface $12b_1$, and subsequently may be formed so that the wall surface $12b_1$ on the opposite side is approached.

Incidentally, as illustrated in FIG. 18(b), the planar shape of both wall surfaces $12b_1$ and $12b_2$ may have a shape like a sign curve having different phase angles, and also in this case, the wall surface in a width direction on both sides of the micro-channel will be disposed asymmetrically.

Furthermore, in place of configurations of unsymmetrical disposition of wall surfaces in width directions on both sides, the wall surfaces positioned in the upper surface and the under surface of the micro-channel may also be disposed asymmetrically, Alternatively, a configuration of unsymmetrical disposition of the wall surface on both sides in the width direction and a configuration of unsymmetrical disposition of the wall surface positioned on both sides and under surface, that is, on both sides in the thickness direction of the substrate may be used in combination.

In any case, since each of the wall surfaces has a unsymmetrical shape on at least one of the both sides in the width direction of the micro-channel, and the both sides in the thickness direction of the substrate, the flow of the micro-droplet generates swirls, leading to sufficient mixing of the micro-droplet. Therefore, the device of the present invention eliminates the necessity for further formation of a large mixing chamber or a coil-like mixing section, resulting in miniaturization of the microfluidic device.

The above-described microfluidic device may be used in, for example, separation and analysis of substances, biochemistry, or, chemical reactions or protein crystallization etc. Although disposable use or replacement after use of only the limited number of times is desirable in the application, permanent use is also possible. In this case use by combination with apparatus, such as dispenser or measuring instrument, is also possible.

Hereinafter, usable materials for the present invention will be described.

As long as the above-described flow path circuit patterns are realized, kinds of materials for the substrate of the above-described microfluidic device are not limited, and inorganic materials and organic materials may be used. The materials that can be used include for example, polydimethylsiloxanes (PDMS), glass, silicones, quartz, thermoplastic resins, hardening resin by light or heat, other resins, metals, ceramics and combination of the above-mentioned materials etc.

As optical responsive gas generating resin compositions that provide optical responsive gas generating agents used in the present invention, resin compositions that include binder resins like thermoplastic resins as a principal component, and that generates gas by optical irradiation may be used without any special limitation. Resin compositions that generates gas by optical irradiation in a wavelength range of 330 to 410 nm are preferred.

The above-described resin composition may be a resin composition including binder resins and gas generating agents that generates gas by optical irradiation.

The binder resins include thermoplastic resins such as polyesters, poly(meth)acrylates, polyethylenes, polypropylenes, polystyrenes, poly-ethers, polyurethanes, polycarbonates, polyamides, polyimides, etc.; acetal resins, such as povals and butyrals; polyoxyalkylene resins etc. having stimulus response gas generation function etc.

As the gas generating agents that generate gas by optical irradiation are not especially limited, and for example, azo compounds, azido compounds, etc.; compounds of polyoxyalkylene resins, photoacid generators, and sodium hydrogencarbonate, etc. may be used. Owing to higher gas generation efficiency, azo compounds and azido compounds are preferably used.

The above-described azo compounds include, for example, 2,2'-azobis(N-butyl-2-methylpropionamide), 2,2'-azobis{2-methyl-N-[1,1-bis(hydroxymethyl)-2-hydroxyethyl]propionamide}, 2,2'-azobis{2-methyl-N-[2-(1-hydroxybutyl)]propionamide}, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), 2,2'-azobis(N-cyclohexyl-2-methylpropionamide), 2,2'-azobis[2-(5-methyl-2-imidazoylin 2-yl)propane]dihydrochloride, 2,2'-azobis[2-(2-imidazoylin 2-yl)propane]dihydrochloride, 2,2'-azobis[2-(2-imidazoylin 2-yl)propane]disulfatedihydrate, 2,2'-azobis[2-(3,4,5,6-tetrahydropyrimidine-2-yl)propane]dihydrochloride, 2,2'-azobis{2-[1-(2-hydroxyethyl)-2-imidazoylin 2-yl]propane}dihydrochloride, 2,2'-azobis[2-(2-imidazoylin 2-yl)propane], 2,2'-azobis(2-methylpropione friend dyne)hydrochloride, 2,2'-azobis(2-aminopropane)dihydrochloride, 2,2'-azobis[N-(2-carboxyacyl)-2-methyl-propioneamidine], 2,2'-azobis{2-[N-(2-carboxyethyl)amidine]propane}, 2,2'-azobis(2-methylpropionamide oxime), dimethyl-2,2'-azobis(2-methylpropionate), dimethyl-2,2'-azobisisobutyrate, 4,4'-azobis(4-cyan carbonic acid), 4,4'-azobis(4-cyanopentanoic acid), 2,2'-azobis(2,4,4-trymethyl pentane) etc. Above all, 2,2'-azobis(N-butyl-2-methylpropionamide), 2,2'-azobis(N-butyl-2-methylpropionamide), and 2,2'-azobis(N-cyclohexyl-2-methylpropionamide) are preferred. These azo compounds generate nitrogen gas by stimulation by light, heat, etc.

The above-described azido compounds include, for example, 3-azidomethyl 3-methyl oxetane, terephthalazide, p-tert-butylbenzazide; polymers having azido groups, such as glycidyl azide polymer obtained by ring opening polymerization of 3-azidomethyl-3-methyl oxetane etc.

As photoacid generators, there may be used photoacid generators, such as bis(cyclohexylsulfonyl)diazomethane, bis(t-butylsulfonyl)diazomethane, bis(p-toluenesulfonyl)diazomethane, triphenylsulfoniumtrifluoromethanesulfonate, dimethyl-4-methylphenylsulfoniumtrifluoromethane sulfonate, diphenyl-2,4,6-trimethyl phenyl sulfoniump-toluenesulfonate etc. diazodisulfone types; diazodisulfone types, such as triphenylsulfonium types; triphenylsulfonium types etc.

Incidentally, publicly known sensitizers may be included in the above-described optical responsive gas generating resin compositions in order to improve response.

Sensitizers include, for example, acetophenones, benzophenone, Michler's ketone, benzyl, benzoin, benzoin ethers, benzyl dimethylketal, benzoyl benzoate, α-acyloxim ester, tetramethylthiuram monosulfide, thioxantone, fatty amines, amines including aromatic group, compounds in which nitrogen forms a part of ring system like piperidine, allylthiourea, o-tolyl thioirea, sodium diethyl dithiophosphate, soluble salts of aromatic sulfinic acids, N,N-disubstituted-p-aminobenzonitrile compounds, tri-n-butylphosphine, N-nitroso hydroxylamine derivatives, oxazolidine compounds, tetrahydro-1,3-oxazine compounds, condensates of formaldehyde or acetaldehyde, and diamine, anthracene (or derivatives thereof), xanthin, N-phenylglycine, phthalocyanine, naphthocyanine, cyanine dye porphyrins, such as thiocyanine (or derivative thereof) etc. These sensitizers may be used independently, and two or more kinds may be used in combination.

In optical irradiation to the optical window, the optical responsive gas generating resin composition within the gas generating chamber generates a gas, and generation of the gas is most accelerated on the surface of the optical responsive gas generating resin composition irradiated with a light. Accordingly, an air layer is preferably formed between the optical responsive gas generating resin composition and the optical window within the gas generating chamber so as to allow easy generation of the gas and easy exhaust of the generated gas from the micro-channel.

Formation of irregularity on the surface of the optical responsive gas generating resin composition gives a larger surface area, and preferably gives consequent easy exhaust of the gas, and furthermore, partial contact at a large number of points between the optical responsive gas generating resin composition and the optical window preferably forms a large number of contact portions and air layers within the gas generating chamber.

Since various samples, diluting solutions, eluants, etc. are used in the microfluidic device, and as a result a large number of micro pumps are needed for one microfluidic device, a plurality of gas generating chambers are preferably formed in the substrate. Since the gas generating chamber needs to be irradiated with light, the gas generating chamber is preferably formed in all over the base material.

Any methods may be used for preparing the trace amount of liquid weighing structure in the present invention, as long as the above-described trace amount of liquid weighing structure is realized. For example, examples of the methods include: machining; transfer method represented by injection molding and compression molding; nano imprint lithography; cast molding; electroforming; dry etching (RIE, IE, IBE, plasma etching, laser etching, laser abrasion, blasting, electric exhaust machining, LIGA, electron beam etching, FAB); wet etching (chemical corrosion); integral moldings, such as optical molding and ceramic spreading; surface Micro-machining by formation of fine structure materials by vapor deposition, sputtering, deposition, and partial removal after layered coating of various substances; a method of formation of grooves after formation of opening parts in sheeted articles of one or more sheets (films, tapes, etc.); a method of formation by dropping and injection using ink-jet or dispenser of materials for flow path circuit pattern etc.

In order to prepare the microfluidic device, masks may be used in the described methods. The mask may have any kind of design, and a plurality of masks may also be used, as long as the microfluidic device can finally be prepared. Usually, the mask is designed so as to give a shape of a flow path projected on a flat surface. In case of a processing being performed on both sides of materials for flow path circuit pattern to be applied, and in case of formation of the flow path using a plurality of components, etc., since processing performed using a plurality of masks or direct processing without use of the mask is possible, the mask does not necessarily need to have a shape of projection of the shape of the final flow path. As mask for shielding of electromagnetic waves used for photo-setting resins etc., materials obtained by coating of chromium to crystals or glasses, or laser baking to films of resins etc. may be mentioned.

The above-described mask may also be manufactured, for example by drawing at least a part of the above-described flow path circuit pattern using a computer and suitable software, and then by printing the drawing to a transparent resin film. The present invention also includes computer readable recording media or program codes for forming the above-described patterns for the flow path circuit pattern, and storage media therefor that is used for manufacturing of the above-described masks drawn by the above-described software or master chips and that stores electronic information of at least a part of the above-described flow path circuit pattern. Suitable recording media here include, for example: magnetic media, such as flexible disks, hard disks, and magnetic tapes; optical discs, semiconductor memory, etc., such as CD-ROM, MO, CD-R, CD-RW, and DVD etc.

In preparing the microfluidic device, the chip may be directly manufactured by the above described methods, and the microfluidic device may also be molded using the above-mentioned device manufactured as a model. Naturally, it is also possible to mold the microfluidic device further using the device as a model.

The microfluidic device in the present invention may have a two-layered structure wherein an upper board and lower board are laminated together. The laminating methods include: adhesion by adhesives, resin junction by primer, diffused junction, anode joining, eutectic bonding, thermal melting, ultrasonic jointing, laser fusing, lamination by solvent and dissolution solvent, bonding by pressure sensitive adhesive tapes, adhesive tapes, compression bonding, and self-adsorbent, physical holding, and combination by irregularity. Incidentally, manufacturing by superposition of multi-layer substrates, while keeping connection configuration, is also possible.

Furthermore, a method by integrated formation of the above-described fluid branching portion and independent flow path without using lamination is also possible. It is possible to form a configuration including a closed volume by integrated molding, such as, in detail, stereolithography.

The length of one side, shape, and thickness of the chip prepared in this way are not limited, and for example, it can be set as any values of 5 mm to 100 mm for one side.

What is claimed is:
1. A microfluidic device having
a substrate; and
a micro-channel structure through which a micro-droplet is transported, the micro-channel structure being formed in the substrate,
the micro-channel structure having a first mixing unit, and a second mixing unit connected to a downstream of the first mixing unit,
each mixing unit comprising:
a first measuring section consisting of a micro-channel having a capacity equal to a volume of a first micro-droplet having a fixed amount, for measuring of a fixed amount of the first micro-droplet;
a second measuring section consisting of a micro-channel having a capacity equal to a volume of a second micro-droplet of a fixed amount, for measuring a fixed amount of the second micro-droplet;
a merging section for merging the first and the second micro-droplets that have been measured in the first and the second measuring section;
a mixing section for mixing the first and the second micro-droplets, the mixing section connected in series to a downstream of the merging section;
an exhausting section for exhausting the mixed droplet obtained by mixing the first and the second micro-droplets;
a first to a third inlet ports and a first to a third outlet ports;
a first micro-channel for connecting the first inlet port and the first outlet port;
a second micro-channel having the merging section, the mixing section, and the exhausting section, the second micro-channel connecting the second inlet port and the second outlet port;
a third micro-channel for connecting the third inlet port and the third outlet port;
an end of the first measuring section being connected to the first micro-channel,
another end of the first measuring section having an opening in the merging section provided in the second micro-channel,
an end of the second measuring section being connected to the third micro-channel,
another end of the second measuring section having an opening in the merging section provided in the second micro-channel,
the second outlet port being connected to the exhausting section,
one of the outlet ports in the first to the third outlet ports of the first mixing unit being connected to the first or the third inlet port of the second mixing unit, wherein the second outlet port of the first mixing unit is connected to and in fluid communication with the first inlet port of the second mixing unit such that liquid exiting the second outlet port enters the first inlet port of the second mixing unit.

2. The microfluidic device, according to claim 1, wherein a micro-droplet mixed in the first mixing unit is used as a fixed amount of the first or the second micro-droplet in the second mixing unit.

3. The microfluidic device according to claim 2, wherein the opening of the end of the first measuring section in the merging section provided in the second micro-channel and the opening of the end of the second measuring section in the merging section provided in the second micro-channel are disposed in different positions with each other in a flowing direction of a micro-droplet in the merging section in the first and/or the second mixing unit.

4. The microfluidic device according to claim 2, wherein a distance between the opening of the end of the first measuring section in the merging section provided in the second micro-channel and the opening of the end of the second measuring section in the merging section provided in the second micro-channel, in the flowing direction of the micro-droplet in the second micro-channel is selected so as to avoid formation of an air bubble between the first micro-droplet supplied to the merging section from the first measuring section and the second micro-droplet supplied to the merging section from the second measuring section, and so as to avoid contact of the first and the second micro-droplet to the outlet opening of the second measuring section, or to the outlet opening of the first measuring section upon exhausting at different timings of the first and the second micro-droplet to the merging, section from the second measuring section.

* * * * *